(12) United States Patent
Ouderkirk et al.

(10) Patent No.: US 11,811,044 B1
(45) Date of Patent: Nov. 7, 2023

(54) ELECTROACTIVE POLYMER DEVICES, SYSTEMS, AND METHODS

(71) Applicant: META PLATFORMS TECHNOLOGIES, LLC, Menlo Park, CA (US)

(72) Inventors: Andrew John Ouderkirk, Kirkland, WA (US); Katherine Marie Smyth, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 26 days.

(21) Appl. No.: 17/207,054

(22) Filed: Mar. 19, 2021

Related U.S. Application Data

(62) Division of application No. 16/059,091, filed on Aug. 9, 2018, now Pat. No. 11,011,739.

(60) Provisional application No. 62/650,254, filed on Mar. 29, 2018, provisional application No. 62/646,900, filed on Mar. 22, 2018.

(51) Int. Cl.
| | |
|---|---|
| *H01M 4/04* | (2006.01) |
| *G02B 27/01* | (2006.01) |
| *H01M 4/60* | (2006.01) |
| *H10N 30/50* | (2023.01) |
| *H10N 30/20* | (2023.01) |

(52) U.S. Cl.
CPC ...... *H01M 4/0428* (2013.01); *G02B 27/0172* (2013.01); *G02B 27/0176* (2013.01); *H01M 4/602* (2013.01); *H10N 30/2027* (2023.02); *H10N 30/50* (2023.02); *G02B 2027/0178* (2013.01)

(58) Field of Classification Search
CPC combination set(s) only.
See application file for complete search history.

(56) References Cited

U.S. PATENT DOCUMENTS

| | | | |
|---|---|---|---|
| 60,109 | A | 11/1866 | Woodward |
| 3,571,555 | A | 3/1971 | Townes et al. |
| 3,797,922 | A | 3/1974 | Plummer |
| 4,477,158 | A | 10/1984 | Pollock et al. |
| 5,154,862 | A | 10/1992 | Reagan et al. |
| 5,225,244 | A | 7/1993 | Aharoni et al. |

(Continued)

FOREIGN PATENT DOCUMENTS

| | | |
|---|---|---|
| JP | 2002243918 A | 8/2002 |
| KR | 10-2011-0107812 A | 10/2011 |

(Continued)

OTHER PUBLICATIONS

Non-Final Office Action received for U.S. Appl. No. 16/035,562 dated Jun. 10, 2021, 36 pages.

(Continued)

*Primary Examiner* — Daniel S Gatewood
(74) *Attorney, Agent, or Firm* — Greenberg Traurig, LLP

(57) ABSTRACT

A method for forming an electroactive device may include (i) depositing a curable material onto a primary electrode, (ii) curing the deposited curable material to form an electroactive polymer element comprising a cured elastomer material, and (iii) depositing an electrically conductive material onto a surface of the electroactive polymer element opposite the primary electrode to form a secondary electrode. The cured elastomer material may have a Poisson's ratio of between approximately 0.1 and approximately 0.35. Various other devices, methods, and systems are also disclosed.

19 Claims, 10 Drawing Sheets

(56) References Cited

U.S. PATENT DOCUMENTS

| | | | |
|---|---|---|---|
| 5,663,779 | A | 9/1997 | Karasawa |
| 5,956,183 | A | 9/1999 | Epstein et al. |
| 6,081,388 | A | 6/2000 | Widl |
| 6,210,678 | B1 | 4/2001 | Richards |
| 6,420,441 | B1 | 7/2002 | Allen et al. |
| 6,747,806 | B2 | 6/2004 | Gelbart |
| 6,918,670 | B2 | 7/2005 | Blum et al. |
| 7,008,054 | B1 | 3/2006 | Kurtin et al. |
| 7,118,219 | B2 | 10/2006 | Itagaki |
| 7,125,508 | B2 | 10/2006 | Ide et al. |
| 7,864,440 | B2 | 1/2011 | Berge |
| 7,866,816 | B2 | 1/2011 | Kurtin |
| 8,441,737 | B2 | 5/2013 | Buch et al. |
| 9,292,085 | B2 | 3/2016 | Bennett et al. |
| 10,187,568 | B1 | 1/2019 | Tran et al. |
| 10,409,089 | B2 | 9/2019 | Pugh et al. |
| 10,698,224 | B1 | 6/2020 | Cooke et al. |
| 10,754,145 | B1 | 8/2020 | Ouderkirk et al. |
| 10,881,287 | B1 | 1/2021 | Ouderkirk et al. |
| 10,928,558 | B1 | 2/2021 | Cooke et al. |
| 10,928,656 | B1 | 2/2021 | Smyth et al. |
| 10,962,791 | B1 | 3/2021 | Ouderkirk et al. |
| 11,011,739 | B1 | 5/2021 | Ouderkirk et al. |
| 11,048,075 | B1 | 6/2021 | Ouderkirk et al. |
| 2003/0003295 | A1 | 1/2003 | Dreher et al. |
| 2003/0054115 | A1 | 3/2003 | Albano et al. |
| 2003/0067245 | A1 | 4/2003 | Pelrine et al. |
| 2003/0083433 | A1 | 5/2003 | James et al. |
| 2003/0128496 | A1 | 7/2003 | Allen et al. |
| 2004/0096672 | A1 | 5/2004 | Lukas et al. |
| 2006/0024976 | A1 | 2/2006 | Waldfried et al. |
| 2006/0073424 | A1 | 4/2006 | Koveshnikov et al. |
| 2006/0228092 | A1 | 10/2006 | Hebrink et al. |
| 2006/0247404 | A1 | 11/2006 | Todd |
| 2007/0035839 | A1 | 2/2007 | Ibuki |
| 2008/0038561 | A1 | 2/2008 | Yoshizawa et al. |
| 2008/0049431 | A1 | 2/2008 | Boek et al. |
| 2008/0084532 | A1 | 4/2008 | Kurtin |
| 2008/0088793 | A1 | 4/2008 | Sverdrup et al. |
| 2008/0123049 | A1 | 5/2008 | Volk |
| 2008/0144185 | A1 | 6/2008 | Wang et al. |
| 2008/0170299 | A1 | 7/2008 | Kawabata |
| 2008/0171431 | A1 | 7/2008 | Yu et al. |
| 2008/0290435 | A1 | 11/2008 | Oliver et al. |
| 2008/0291394 | A1 | 11/2008 | Ishak |
| 2009/0015786 | A1 | 1/2009 | Harris |
| 2009/0027778 | A1 | 1/2009 | Wu et al. |
| 2009/0096106 | A1 | 4/2009 | Vrtis et al. |
| 2009/0289529 | A1 | 11/2009 | Ito et al. |
| 2009/0304924 | A1 | 12/2009 | Gadgil |
| 2010/0075056 | A1 | 3/2010 | Axisa et al. |
| 2010/0109486 | A1 | 5/2010 | Polyakov et al. |
| 2010/0168409 | A1 | 7/2010 | Fujita |
| 2010/0202054 | A1 | 8/2010 | Niederer |
| 2010/0238400 | A1 | 9/2010 | Volk |
| 2011/0075096 | A1 | 3/2011 | Ishak et al. |
| 2011/0085131 | A1 | 4/2011 | Gupta et al. |
| 2011/0096411 | A1 | 4/2011 | Henriksen et al. |
| 2011/0149410 | A1 | 6/2011 | Blum |
| 2011/0176105 | A1 | 7/2011 | Harris |
| 2011/0179861 | A1 | 7/2011 | Grange et al. |
| 2011/0235326 | A1 | 9/2011 | Yeh et al. |
| 2011/0294305 | A1 | 12/2011 | Jacobs et al. |
| 2012/0029416 | A1 | 2/2012 | Parker et al. |
| 2012/0032559 | A1 | 2/2012 | Hino et al. |
| 2012/0041553 | A1 | 2/2012 | Gupta et al. |
| 2012/0044571 | A1 | 2/2012 | Mukawa |
| 2012/0063000 | A1 | 3/2012 | Batchko et al. |
| 2012/0087015 | A1 | 4/2012 | Nibauer et al. |
| 2012/0092775 | A1 | 4/2012 | Duston et al. |
| 2012/0170920 | A1 | 7/2012 | Moreau et al. |
| 2012/0229754 | A1 | 9/2012 | Iyer et al. |
| 2012/0250151 | A1 | 10/2012 | Lee et al. |
| 2012/0287512 | A1 | 11/2012 | Egan et al. |
| 2013/0171546 | A1 | 7/2013 | White et al. |
| 2013/0176628 | A1 | 7/2013 | Batchko et al. |
| 2013/0300635 | A1 | 11/2013 | White et al. |
| 2014/0009039 | A1 | 1/2014 | Jenninger et al. |
| 2014/0078586 | A1 | 3/2014 | Spurgeon et al. |
| 2014/0153102 | A1 | 6/2014 | Chang |
| 2014/0186215 | A1 | 7/2014 | Shinta et al. |
| 2014/0227548 | A1 | 8/2014 | Myrick |
| 2014/0300857 | A1 | 10/2014 | Cohen-Tannoudji et al. |
| 2014/0312737 | A1 | 10/2014 | Jenninger et al. |
| 2015/0062719 | A1 | 3/2015 | Kyung et al. |
| 2015/0116656 | A1 | 4/2015 | Stevens et al. |
| 2015/0138110 | A1 | 5/2015 | Yairi et al. |
| 2015/0146161 | A1 | 5/2015 | Rigato et al. |
| 2015/0302990 | A1 | 10/2015 | Ghosh et al. |
| 2015/0323812 | A1 | 11/2015 | Ishak et al. |
| 2016/0004099 | A1 | 1/2016 | Steven et al. |
| 2016/0091635 | A1 | 3/2016 | Ibuki et al. |
| 2016/0187985 | A1 | 6/2016 | Lim et al. |
| 2017/0021385 | A1 | 1/2017 | Smith et al. |
| 2017/0045649 | A1 | 2/2017 | Bolis |
| 2017/0160600 | A1 | 6/2017 | Galstian et al. |
| 2017/0177106 | A1 | 6/2017 | Kihara |
| 2017/0184848 | A1 | 6/2017 | Vallius |
| 2017/0188021 | A1 | 6/2017 | Lo et al. |
| 2017/0192595 | A1 | 7/2017 | Choi et al. |
| 2017/0261653 | A1 | 9/2017 | Peyman |
| 2017/0299956 | A1 | 10/2017 | Holland et al. |
| 2017/0317269 | A1 | 11/2017 | Zhang et al. |
| 2017/0336641 | A1 | 11/2017 | Von Und Zu Liechtenstein |
| 2018/0255250 | A1 | 9/2018 | Price et al. |
| 2018/0275394 | A1 | 9/2018 | Yeoh et al. |
| 2018/0335649 | A1 | 11/2018 | Tsai |
| 2019/0173128 | A1 | 6/2019 | Visco et al. |
| 2019/0243123 | A1 | 8/2019 | Bohn |
| 2019/0296218 | A1 | 9/2019 | Ouderkirk et al. |
| 2019/0302479 | A1 | 10/2019 | Smyth et al. |
| 2020/0166742 | A1 | 5/2020 | Peyman |
| 2020/0251709 | A1 | 8/2020 | Lee et al. |

FOREIGN PATENT DOCUMENTS

| | | |
|---|---|---|
| KR | 101675093 B1 | 11/2016 |
| WO | 2008/156166 A1 | 12/2008 |
| WO | 2010/078666 A1 | 7/2010 |
| WO | 2010/104904 A2 | 9/2010 |
| WO | 2019/183431 A1 | 9/2019 |
| WO | 2019/190887 A1 | 10/2019 |

OTHER PUBLICATIONS

Non-Final Office Action received for U.S. Appl. No. 16/016,428 dated Jun. 16, 2021, 43 pages.
Non-Final Office Action received for U.S. Appl. No. 16/013,837 dated Jan. 23, 2020, 22 pages.
Notice of Allowance received for U.S. Appl. No. 16/013,837 dated Apr. 14, 2020, 14 pages.
Preinterview First Office Action received for U.S. Appl. No. 15/992,731 dated Sep. 27, 2019, 17 pages.
Final Office Action received for U.S. Appl. No. 15/992,731 dated Jun. 2, 2020, 25 pages.
Non-Final Office Action received for U.S. Appl. No. 15/992,731 dated Aug. 24, 2020, 27 pages.
Examiner-Initiated Interview Summary received for U.S. Appl. No. 16/008,635 dated Apr. 20, 2020, 3 pages.
Notice of Allowance received for U.S. Appl. No. 16/008,635 dated May 4, 2020, 32 pages.
International Preliminary Report on Patentability received for PCT Application Serial No. PCT/US2019/023484 dated Oct. 1, 2020, 8 pages.
International Search Report and Written Opinion received for PCT Application Serial No. PCT/US2019/023485 dated Jul. 4, 2019, 11 pages.
Non-Final Office Action received for U.S. Appl. No. 16/106,945 dated Apr. 16, 2020, 59 pages.
Non-Final Office Action received for U.S. Appl. No. 16/041,634 dated Jul. 30, 2020, 24 pages.

(56) References Cited

OTHER PUBLICATIONS

Notice of Allowance received for U.S. Appl. No. 16/041,634 dated Aug. 28, 2020, 31 pages.
Preinterview First Office Action received for U.S. Appl. No. 16/018,752 dated Dec. 16, 2019, 19 pages.
Preinterview First Office Action received for U.S. Appl. No. 16/018,746 dated Jul. 14, 2020, 20 pages.
Notice of Allowance Action received for U.S. Appl. No. 16/018,746 dated Sep. 17, 2020, 24 pages.
Preinterview First Office Action received for U.S. Appl. No. 16/021,580 dated Aug. 4, 2020, 48 pages.
Press Kit Home, "Adaptive glasses", accessed at http://tvc.utah.edu, as accessed on Mar. 13, 2018, 5 pages.
Billah et al., "Microstructure Evolution and Electrical Characterization of Lanthanum doped Barium Titanate (BaTi03) Ceramics", International Conference on Mechanical Engineering, AIP Cont. Proc. 1754, accessed on Jul. 12, 2016, pp. 030006-1-030006-7.
Cao et al., Grain Size and Domain Size Relations in Bulk Ceramic Ferroelectric Materials, J. Phys. Chem Solids vol. 57, No. 10, pp. 1499-1505, 1996.
Ding et al., "Surface profiling of an aspherical liquid lens with a varied thickness membrane," Optics Express 3122-3132, vol. 25, No. 4 (Feb. 6, 2017).
He et al., Linear Electro-Optic Properties of Orthorhombic PZN-8%PT Single Crystal, IEEE Transactions on Ultrasonics, Ferroelectrics, and Frequency Control, vol. 58, No. 6 (Jun. 1, 2011).
Knapp et al., "Understanding Zirconia Crown Esthetics and Optical Properties" Inclusive magazine accessed at http://glidewelldental.com/education/inclusive-dental-implant-magazine-volume-2-issue-4/, as accessed on Jun. 12, 2018, vol. 2, Issue 4, 17 pages.
Optotune, "Focus tunable lenses", accessed at http://www.optotune.com/technology/focus-tunable-lenses, accessed on Mar. 13, 2018, 2 pages.
Polight, "How does it work", accessed at http://www.polight.com/technology-and-products/how-does-it-work/default.aspx, accessed on Mar. 13, 2018, 3 pages.
UZOOM Adlens, "Adjustable Lens Glasses: How They Work", accessed at https://adlens.com/how-it-works/, accessed an Mar. 28, 2018, 9 pages.
Piezo Technology, "Highly Reliable Multilayer Piezo Actuators", accessed on https://www.piceramic.com/en/piezo-technology/picma/, accessed on Mar. 14, 2018, 8 pages.
Piezo Technology, "Displacement Modes of Piezoelectric Actuators", accessed on https://www.piceramic.com/en/piezo-technology/properties-piezo-actuators/displacement-modes/, accessed on Mar. 14, 2018, 12 pages.
Jiang et al., "Transparent Electro-Optic Ceramics and Devices", Proceedings vol. 5644, Optoelectronic devices and integration, accessed at https://doi.org/10.1117/12.582105, Jan. 17, 2005, 15 Pages.
Keplinger et al., "Stretchable, Transparent, Ionic Conductors", Science Magazine, vol. 341, DOI:10.1126/science.1240228, Accessed on Aug. 30, 2013, pp. 984-987.
Kong et al., "Transparent Ceramic Materials", Transparent Ceramics, Topics in Mining, Metallurgy, and Materials Engineering, Ch. 2, DOI: 10.1007/978-3-319-18956-7_2, Springer international Publishing Switzerland 2015, pp. 29-91.
Patra et al., "Comparison on Optical Properties of Pure and Doped Lithium Tetraborate Single Crystals and Glasses", Solid State Physics: Proceedings of the 56th DAE Solid State Physics Symposium 2011, AIP Conf. Proc. 1447, Dec. 11, 2012, pp. 1335-1336.
Riegler et al., "Index Matching Silicone for High Brightness LED Packaging", IMAPS International Conference on Device Packaging Mar. 13-16, Scottsdale AZ., Accessed on Mar. 18, 2005, 17 Pages.
Shian et al., Tunable Lenses using Transparent Dielectric Elastomer Actuators, Optics Express, vol. 21, No. 7 (Apr. 2, 2013).
Hocking, L.M., "The effect of slip on the motion of a sphere close to a wall and of two adjacent spheres", Journal of Engineering Math., vol. 7 (1973), pp. 207-221.

Nang et al., "A Highly Stretchable, Transparent, and Conductive Polymer", Science Advances vol. 3, No. 3, e1602076, Mar. 10, 2017, pp. 1-10.
APC International, Lid., "Piezoelectric Materials, New Materials, Piezo theory", accessed at www.americanpiezo.com/knowledge-center/piezo-theory/new-materials/html, accessed on Mar. 15, 2018, 1 page.
Zhao et al., "Spherical aberration free liquid-filled tunable lens with variable thickness membrane," Optics Express vol. 23, No. 16, accessed at https://doi.org/10.1364/0.23.021264, accessed on Aug. 5, 2015, pp. 21264-21278.
Andrew J. Ouderkirk, et al.; Apparatuses, Systems, and Methods for Adjusting Fluid Lenses; U.S. Appl. No. 16/008,635, filed Jun. 14, 2018.
Katherine Marie Smyth, et al.; Optical Lens Assemblies, Head-Mounted Displays, and Related Methods; U.S. Appl. No. 16/021,650, filed Jun. 28, 2018.
Andrew John Ouderkirk, et al.; Multi-Element Prescription Lenses With Eye-Tracking; U.S. Appl. No. 16/041,634, filed Jul. 20, 2018.
Andrew John Ouderkirk, et al.; Electroactive Polymer Devices and Nanovoided Polymer Materials and Methods and Systems for Fabrication Thereof; U.S. Appl. No. 16/106,945; filed Aug. 21, 2018.
Andrew John Ouderkirk, et al.; Nanovoided Electroactive Polymer Devices, Systems, and Methods; U.S. Appl. No. 16/041,858, filed Jul. 23, 2018.
Andrew John Ouderkirk, et al.; Electroactive Polymer Devices, Systems, and Methods; U.S. Appl. No. 16/059,091, filed Aug. 9, 2018.
Andrew John Ouderkirk, et al.; Optical Devices, Systems, and Methods of Manufacturing; U.S. Appl. No. 32/646,900, filed Mar. 22, 2018.
Andrew John Ouderkirk, et al.; Optical Devices, Systems, and Methods of Manufacturing; U.S. Appl. No. 32/650,254, filed Mar. 29, 2018.
Katherine Marie Smyth, et al.; Optical Lens Assemblies and Related Methods; U.S. Appl. No. 16/018,746, filed Jun. 26, 2018.
Katherine Marie Smyth, et al.; Systems and Methods for Actuation of Asymmetric Optical Elements; U.S. Appl. No. 15/992,731, filed May 30, 2018.
Andrew John Ouderkirk, et al.; Optical Lens Assemblies and Related Methods; U.S. Appl. No. 16/018,752, filed Jun. 26, 2018.
John M. Cooke, et al.; Optical Lens Assemblies, Head-Mounted Displays, and Methods of Altering Optical Properties of Optical Lens Assemblies; U.S. Appl. No. 16/013,837, filed Jun. 20, 2018.
Katherine Marie Smyth, et al.; Optical Lens Assemblies, Head-Mounted Displays, and Related Methods; U.S. Appl. No. 16/016,428, filed Jun. 22, 2018.
Final Office Action dated Sep. 21, 2020 for U.S. Appl. No. 16/059,091, filed Aug. 9, 2018, 18 Pages.
Guha I.F., et al., "Creating Nanoscale Emulsions Using Condensation," Nature Communications, Published: Nov. 8, 2017, vol. 8, Article 1371, pp. 1-7.
Non-Final Office Action dated Apr. 8, 2020 for U.S. Appl. No. 16/059,091, filed Aug. 9, 2018, 54 Pages.
John M. Cooke, et al.; Optical Lens Assemblies, Head-Mounted Displays, and Related Methods; U.S. Appl. No. 16/021,580, filed Jun. 28, 2018.
Andrew John Ouderkirk, et al.; Electroactive Polymer Devices, Systems, and Methods; U.S. Appl. No. 16/035,562, filed Jul. 13, 2018.
"Adjustable Reading Glasses," Retrieved from internet URL: https://adlens.com/.
International Preliminary Report on Patentability received for PCT Application Serial No. PCT/US2019/023485 dated Oct. 8, 2020, 8 pages.
Merriam-Webster, "Porosity", URL: https://www.merriam-webster.com/dictionary/porosity, retrieved on Apr. 8, 2020, pp. 1-8.
International Search Report and Written Opinion received for PCT Application Serial No. PCT/US2019/023484 dated Jul. 3, 2019, 9 pages.
Notice of Allowance received for U.S. Appl. No. 15/972,794 dated Oct. 16, 2020, 22 pages.

(56) References Cited

OTHER PUBLICATIONS

Notice of Allowance received for U.S. Appl. No. 15/992,731 dated Nov. 18, 2020, 37 pages.
Final Office Action received for U.S. Appl. No. 16/106,945 dated Nov. 24, 2020, 94 pages.
Final Office Action received for U.S. Appl. No. 16/018,752 dated Nov. 30, 2020, 41 pages.
Notice of Allowance received for U.S. Appl. No. 16/018,746 dated Nov. 3, 2020, 39 pages.
Notice of Allowance received for U.S. Appl. No. 16/021,580 dated Dec. 9, 2020, 68 pages.
Preinterview First Office Action received for U.S. Appl. No. 16/021,650 dated Feb. 1, 2021, 47 pages.
Gurvich, Mark R., "On Characterization of Anisotropic Elastomeric Materials for Structural Analysis", Rubber Chemistry and Technology, vol. 77, No. 1, 2004, pp. 115-130.
Non-Final Office Action received for U.S. Appl. No. 16/106,945 dated Mar. 30, 2021, 111 pages.
Notice of Allowance received for U.S. Appl. No. 16/018,752 dated Mar. 10, 2021, 32 pages.
Communication pursuant to Article 94(3) EPC received for EP Patent Application Serial No. 19715707.6 dated Mar. 22, 2021, 5 page.
Non-Final Office Action received for U.S. Appl. No. 16/016,428 dated Mar. 12, 2021, 56 pages.

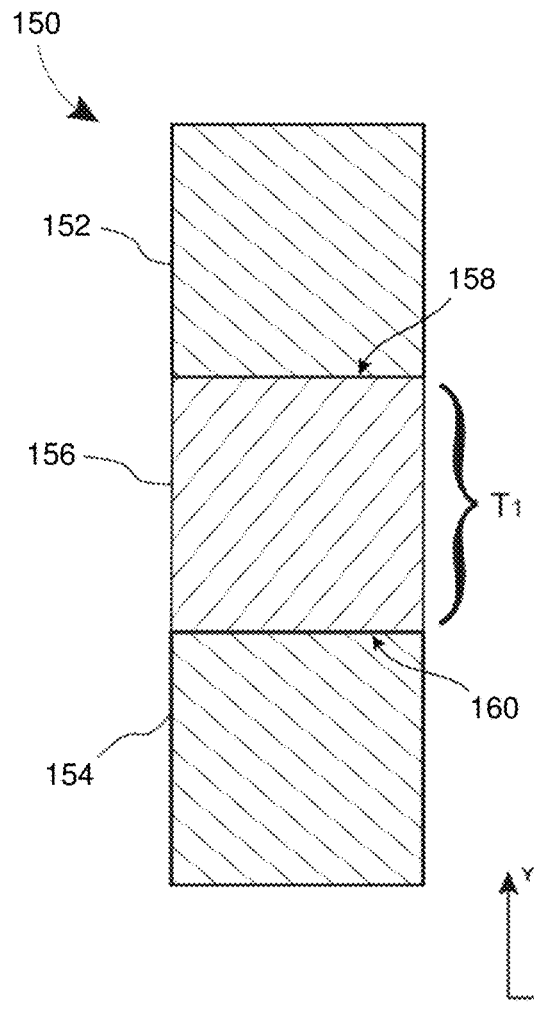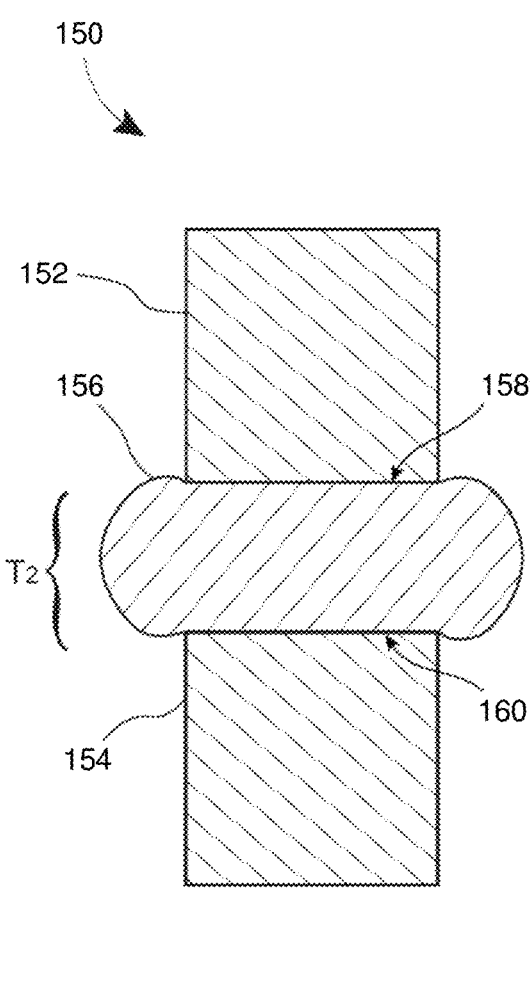
*FIG. 1B*  *FIG. 1C*

ELECTROACTIVE POLYMER DEVICES, SYSTEMS, AND METHODS

CROSS REFERENCE TO RELATED APPLICATION

This application is a non-provisional divisional application which claims the benefit of U.S. application Ser. No. 16/059,091 filed 9 Aug. 2018, which claims the benefit of U.S. Provisional Application No. 62/646,900 filed 22 Mar. 2018 and U.S. Provisional Application No. 62/650,254 filed 29 Mar. 2018, the disclosures of each of which are incorporated, in their entirety, by this reference.

BACKGROUND

Augmented reality (AR) and virtual reality (VR) eyewear devices or headsets may enable users to experience events, such as interacting with people in a computer-generated simulation of a three-dimensional world or viewing data superimposed on a real-world view. AR/VR eyewear devices and headsets may also be used for purposes other than recreation. For example, governments may use such devices for military training simulations, doctors may use such devices to practice surgery, and engineers may use such devices them as visualization aids.

AR/VR eyewear devices and headsets typically include some form of optical system or device, such as an optical lens assembly configured to focus or direct light from the device's display and/or the real world to the user's eyes. Thus, there is a need for improving such optical systems.

SUMMARY

As will be described in greater detail below, the instant disclosure describes various electroactive devices that include electroactive polymer materials, and associated systems and methods. In various embodiments, an electroactive device may include: (i) a primary electrode, a secondary electrode overlapping at least a portion of the primary electrode, and a tertiary electrode overlapping at least a portion of the secondary electrode, (ii) a first electroactive polymer element including a first elastomer material disposed between and abutting the primary electrode and the secondary electrode, and (iii) a second electroactive polymer element including a second elastomer material disposed between and abutting the secondary electrode and the tertiary electrode. In some examples, the first elastomer material and the second elastomer material may each have a Poisson's ratio of approximately 0.35 or less. Additionally, (i) the first electroactive polymer element may be deformable from an initial state to a deformed state when a first voltage is applied between the primary electrode and the secondary electrode, and (ii) the second electroactive polymer element may be deformable, in conjunction with deformation of the first electroactive polymer element, from an initial state to a deformed state when a second voltage is applied between the secondary electrode and the tertiary electrode.

In some embodiments, a primary common electrode may be electrically coupled to the primary electrode and the tertiary electrode, and a secondary common electrode may be electrically coupled to the secondary electrode. In some embodiments, (i) at least one additional electroactive polymer element may be disposed on a side of the tertiary electrode opposite the second electroactive polymer element, the at least one additional electroactive polymer element overlapping the first electroactive polymer element and the second electroactive polymer element, and (ii) at least one additional electrode may be disposed abutting a surface of one of the at least one additional electroactive polymer element that faces away from the second electroactive polymer element.

In another example, the first electroactive polymer element may have a maximum thickness in an undeformed state and a compressed thickness in the deformed state, and the second electroactive polymer element may have a maximum thickness in an undeformed state and a compressed thickness in the deformed state. In some examples, (i) the first elastomer material may have a density, when the first electroactive polymer element is in the undeformed state, that is approximately 90% or less of a density of the first elastomer material when the first electroactive polymer element is in the deformed state, and (ii) the second elastomer material may have a density, when the second electroactive polymer element is in the undeformed state, that is approximately 90% or less of a density of the second elastomer material when the second electroactive polymer element is in the deformed state. In other examples, the first elastomer material may exhibit a strain of at least approximately 10% when a voltage is applied between the primary electrode and the secondary electrode, and the second elastomer material may exhibit a strain of at least approximately 10% when a voltage is applied between the secondary electrode and the tertiary electrode.

In further examples, at least one of the first electroactive polymer element or the second electroactive polymer element may include particles of a material having a high dielectric constant, the particles having an average diameter between approximately 10 nm and approximately 1000 nm. In some embodiments, the material having the high dielectric constant may include barium titanate.

A corresponding method may include (i) depositing a curable material onto a primary electrode, (ii) curing the deposited curable material to form an electroactive polymer element including a cured elastomer material, and (iii) depositing an electrically conductive material onto a surface of the electroactive polymer element opposite the primary electrode to form a secondary electrode. In some examples, the cured elastomer material may have a Poisson's ratio of approximately 0.35 or less. According to some embodiments, the method may further include (i) depositing an additional curable material onto a surface of the secondary electrode opposite the electroactive polymer element, (ii) curing the deposited additional curable material to form a second electroactive polymer element including a second cured elastomer material, and (iii) depositing an additional electrically conductive material onto a surface of the second electroactive polymer element opposite the secondary electrode to form a tertiary electrode.

In some embodiments, the cured elastomer material may include at least one non-polymeric component in a plurality of defined regions and the method may further include removing at least a portion of the at least one non-polymeric component from the cured elastomer material to form a nanovoided polymer material. According to at least one example, the method may include vaporizing the curable material, where depositing the curable material may include depositing the vaporized curable material onto the primary electrode. In other examples, depositing the curable material may include printing the curable material onto the primary electrode. The method may also include combining the curable material with at least one non-curable component to form a mixture including the curable material and the at least one non-curable component on the primary electrode. The method may further include combining the curable material with particles of a material having a high dielectric constant.

According to some embodiments, a method may include positioning a curable material between a first electrically conductive material and a second electrically conductive material, and curing the positioned curable material to form an electroactive polymer element including a cured elastomer material. In some examples, the cured elastomer material may have a Poisson's ratio of approximately 0.35 or less. In some examples, at least one of the first electrically conductive material or the second electrically conductive material may include a curable electrically conductive material, and the method may further include curing the at least one of the first electrically conductive material or the second electrically conductive material to form an electrode. In this example, curing the at least one of the first electrically conductive material or the second electrically conductive material may include curing the at least one of the first electrically conductive material or the second electrically conductive material during curing of the positioned curable material.

In various embodiments, the curable material and at least one of the first electrically conductive material or the second electrically conductive material may be flowable during positioning of the curable material between the first electrically conductive material and the second electrically conductive material. The method further includes flowing the curable material and the at least one of the first electrically conductive material or the second electrically conductive material simultaneously onto a substrate.

While the exemplary embodiments described herein are susceptible to various modifications and alternative forms, specific embodiments will be described in detail herein. However, the exemplary embodiments described herein are not intended to be limited to the particular forms disclosed. Rather, the instant disclosure covers all modifications, equivalents, and alternatives falling within this disclosure.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 1B shows a diagram of another example electroactive device in accordance with some embodiments of the disclosure.

FIG. 1C shows a diagram of the example electroactive device of FIG. 1B in a compressed state in accordance with some embodiments of the disclosure.

Figure 1A:
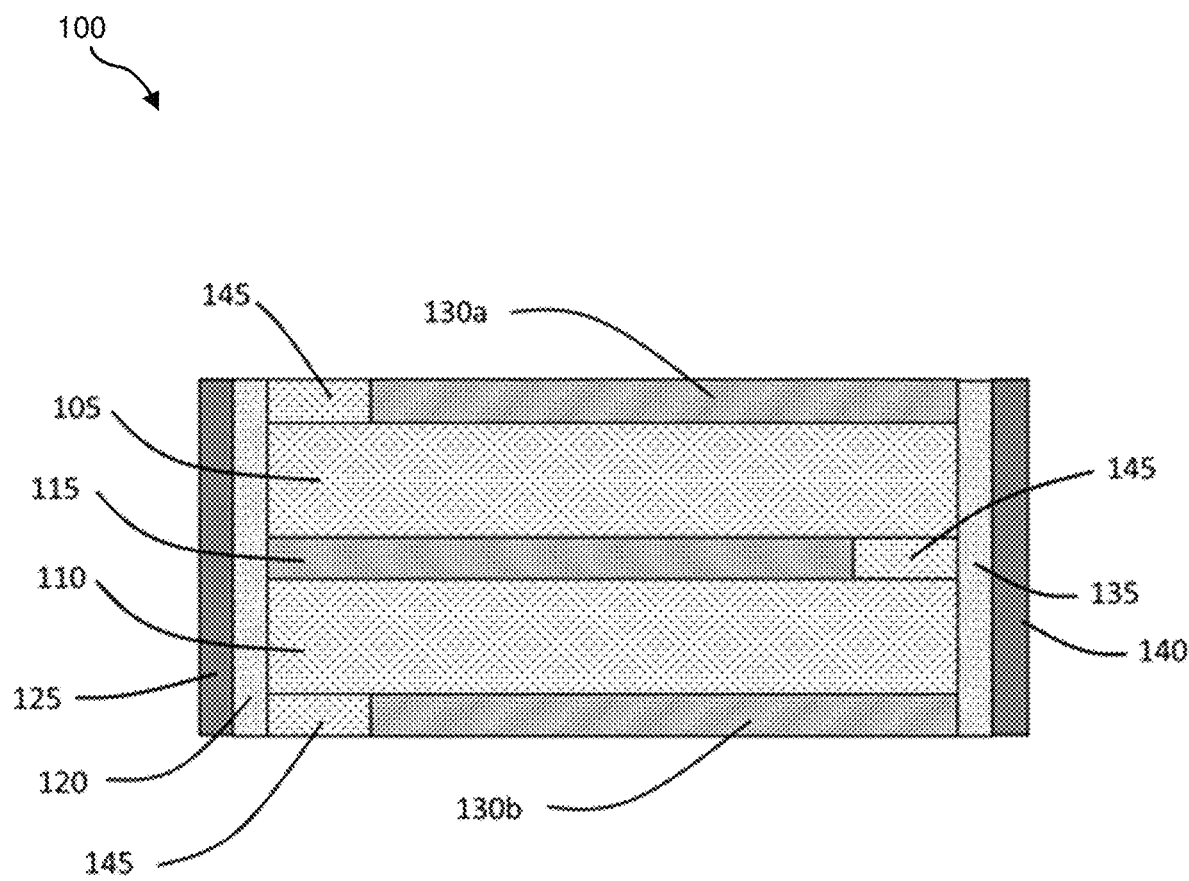
FIG. 1A shows a diagram of an example electroactive device (e.g., an actuator or an energy harvesting device), in accordance with some embodiments of the disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

Embodiments of the disclosure are directed to electroactive devices that may be used to actuate deformable optical elements in optical assemblies (e.g., lens systems). Such electroactive devices may convert electrical energy to mechanical energy (e.g., an actuator), but may also be configured to convert mechanical energy to electrical energy (e.g., an energy harvesting device). Examples of electroactive devices may include, without limitation, actuators, sensors, microelectromechanical devices, and/or any other suitable devices. In various embodiments, electroactive devices may include paired electrodes, which allow the creation of the electrostatic field that forces constriction of the electroactive polymer. Such electrodes may include relatively thin, electrically conductive layers or elements and may be of a non-compliant or compliant nature. Any suitable materials may be utilized in the electrodes, including electrically conductive materials suitable for use in thin-film electrodes, such as, for example, aluminum, transparent conductive oxides, silver, indium, gallium, zinc, carbon nanotubes, carbon black, and/or any other suitable materials formed by vacuum deposition, spray, adhesion, and/or any other suitable technique either on a non-electroactive polymer layer or directly on the electroactive polymer surface itself. In some embodiments, the electrode or electrode layer may be self-healing, such that damage from local shorting of a circuit can be isolated. Suitable self-healing electrodes may include thin films of metals, such as, for example, aluminum.

In some embodiments, an electroactive device may include a stack of at least two electroactive polymer elements (e.g., elastomeric polymer elements) that are layered, with electrodes abutting opposing surfaces of each of the electroactive polymer elements. In some embodiments, the electroactive polymer elements may be driven by adjacent pairs of electrodes. As described below, electrodes may optionally be electrically connected to at least one adjacent common electrode extending along a lateral periphery of the stack via at least one schoopage (i.e., contact) layer.

In some examples, an "electrode," as used herein, may refer to a conductive material, usually a film or a layer. The electrode may be self-healing, such that when an area of an active layer (e.g., a electroactive polymer element) shorts out, the electrode may be able to isolate the damaged area. As used herein, "electroactive polymers" may refer to polymers that exhibit a change in size or shape when stimulated by an electric field. Some electroactive polymers may find limited applications due to a low breakdown voltage of the polymers with respect to the operating voltage used by electroactive devices (e.g., actuators) that use the polymers. Accordingly, electroactive devices with reduced operating voltages and higher energy densities may be useful for many applications. In some examples, an electroactive polymer may include a deformable polymer that may be symmetric with regard to electrical charge (e.g., polydimethylsiloxane (PDMS), acrylates, etc.) or asymmetric (e.g., poled polyvinylidene fluoride (PVDF) or its copolymers such as poly (vinylidenefluoride-co-trifluoroethylene) (PVDF-TrFE)). Additional examples of polymer materials forming electroactive polymer materials may include, without limitation, styrenes, polyesters, polycarbonates, epoxies, halogenated polymers, such as PVDF, copolymers of PVDF, such as PVDF-TrFE, silicone polymers, and/or any other suitable polymer materials. Such materials may have any suitable dielectric constant or relative permittivity, such as, for example, a dielectric constant ranging from approximately 2 to approximately 30.

In the presence of an electrostatic field, an electroactive polymer may deform (e.g., compress, elongates, bends, etc.) according to the strength of that field. Generation of such a field may be accomplished, for example, by placing the electroactive polymer between two electrodes, each of which is at a different potential. As the potential difference (i.e., voltage difference) between the electrodes is increased (e.g., from zero potential) the amount of deformation may also increase, principally along electric field lines. This deformation may achieve saturation when a certain electrostatic field strength has been reached. With no electrostatic field, the electroactive polymer may be in its relaxed state undergoing no induced deformation, or stated equivalently, no induced strain, either internal or external.

The physical origin of the compressive nature of electroactive polymers in the presence of an electrostatic field (E-field), being the force created between opposite electric charges, is that of the Maxwell stress, which is expressed mathematically with the Maxwell stress tensor. The level of strain or deformation induced by a given E-field is dependent on the square of the E-field strength, the dielectric constant of the electroactive polymer, and on the elastic compliance of the material in question. Compliance in this case is the change of strain with respect to stress or, equivalently, in more practical terms, the change in displacement with respect to force.

In some embodiments, the electroactive polymer elements may include an elastomer having an effective Poisson's ratio of less than approximately 0.35 and an effective uncompressed density that is less than approximately 90% of the elastomer when densified. In some examples, the term "effective Poisson's ratio" may refer to the negative of the ratio of transverse strain (e.g., strain in a first direction) to axial strain (e.g., strain in a second direction) in a material. In some embodiments, the electroactive polymer elements may include a nanovoided polymer material.

Methods of forming an electroactive device include forming electrodes and electroactive polymer elements sequentially (e.g., via vapor deposition, coating, printing, etc.) or simultaneously (e.g., via co-flowing, coextrusion, slot die coating, etc.). Alternatively, the electroactive polymer elements may be deposited using initiated chemical vapor deposition (iCVD), where, for example, suitable monomers of the desired polymers may be used to form the desired coating. In some embodiments, monomers, oligomers, and/or prepolymers for forming the electroactive polymer elements may optionally be mixed with a solvent and the solvent may be removed from the electroactive polymer element during and/or following curing to form nanovoids within the electroactive polymer element.

Figure 2:
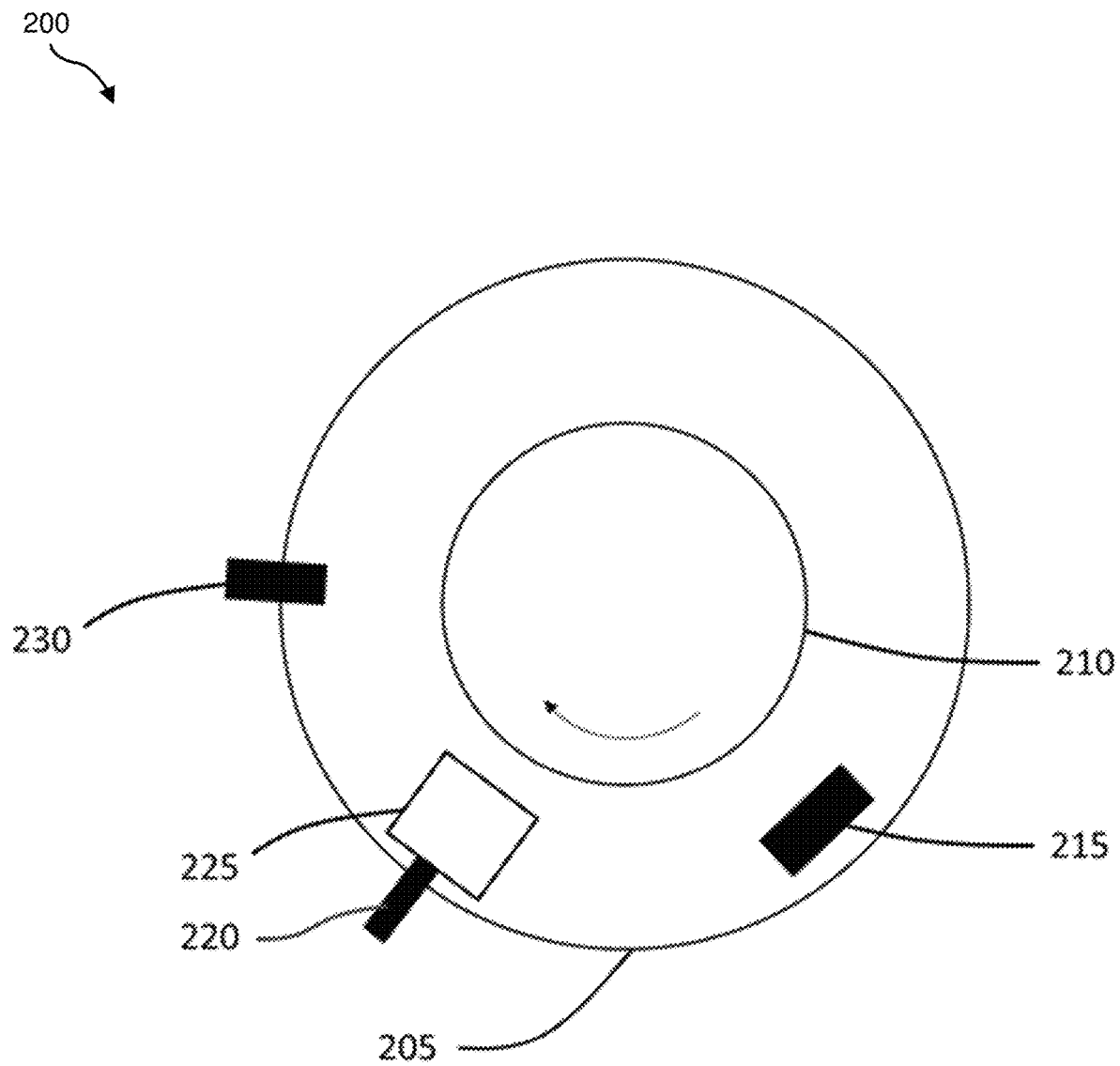
FIG. 2 shows a diagram of an example apparatus for the fabrication of an electroactive device, in accordance with some embodiments of the disclosure.
Figure 3:
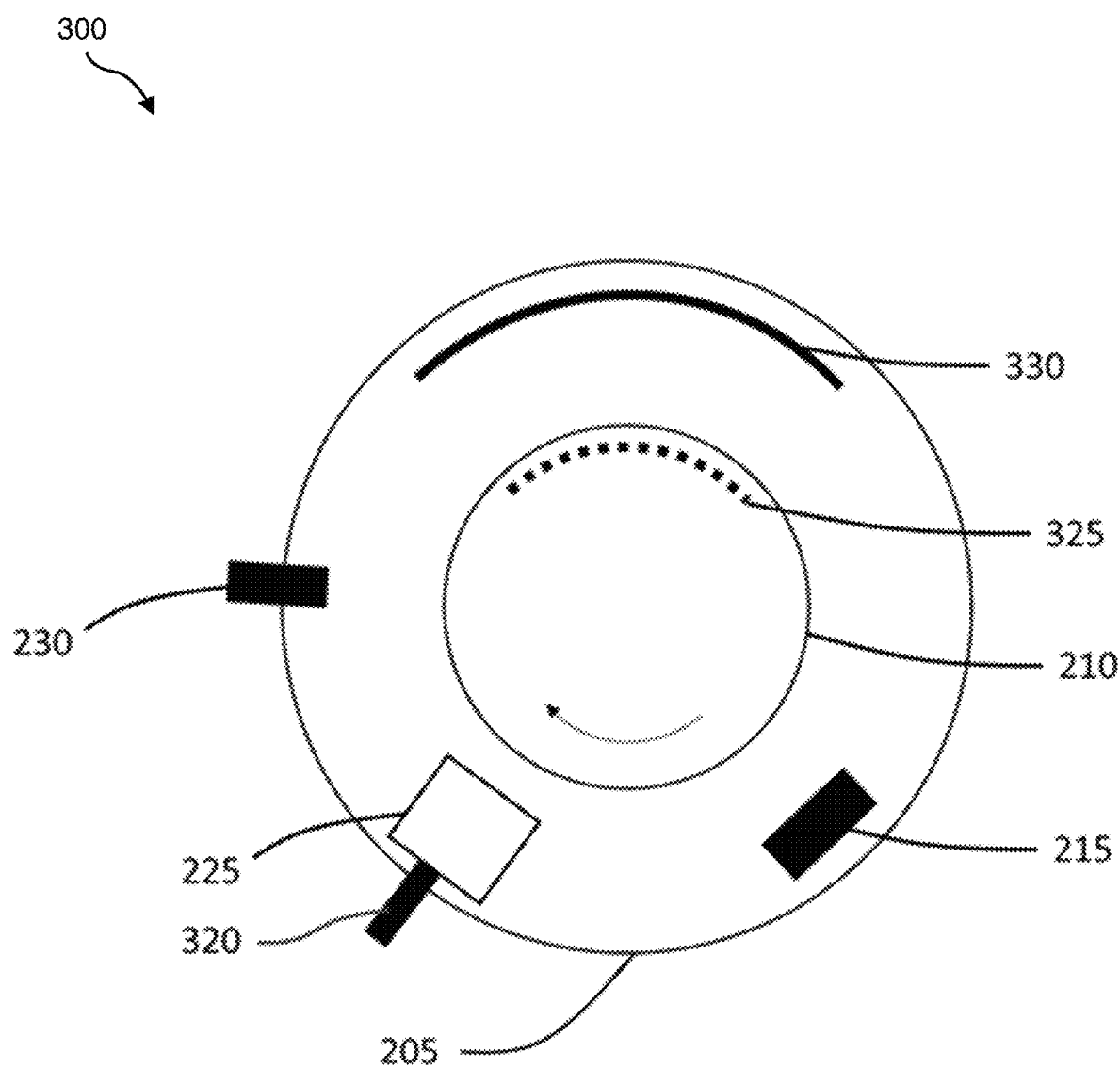
FIG. 3 shows another diagram of an example apparatus for the fabrication of an electroactive device, in accordance with some embodiments of the disclosure.
Figure 4:
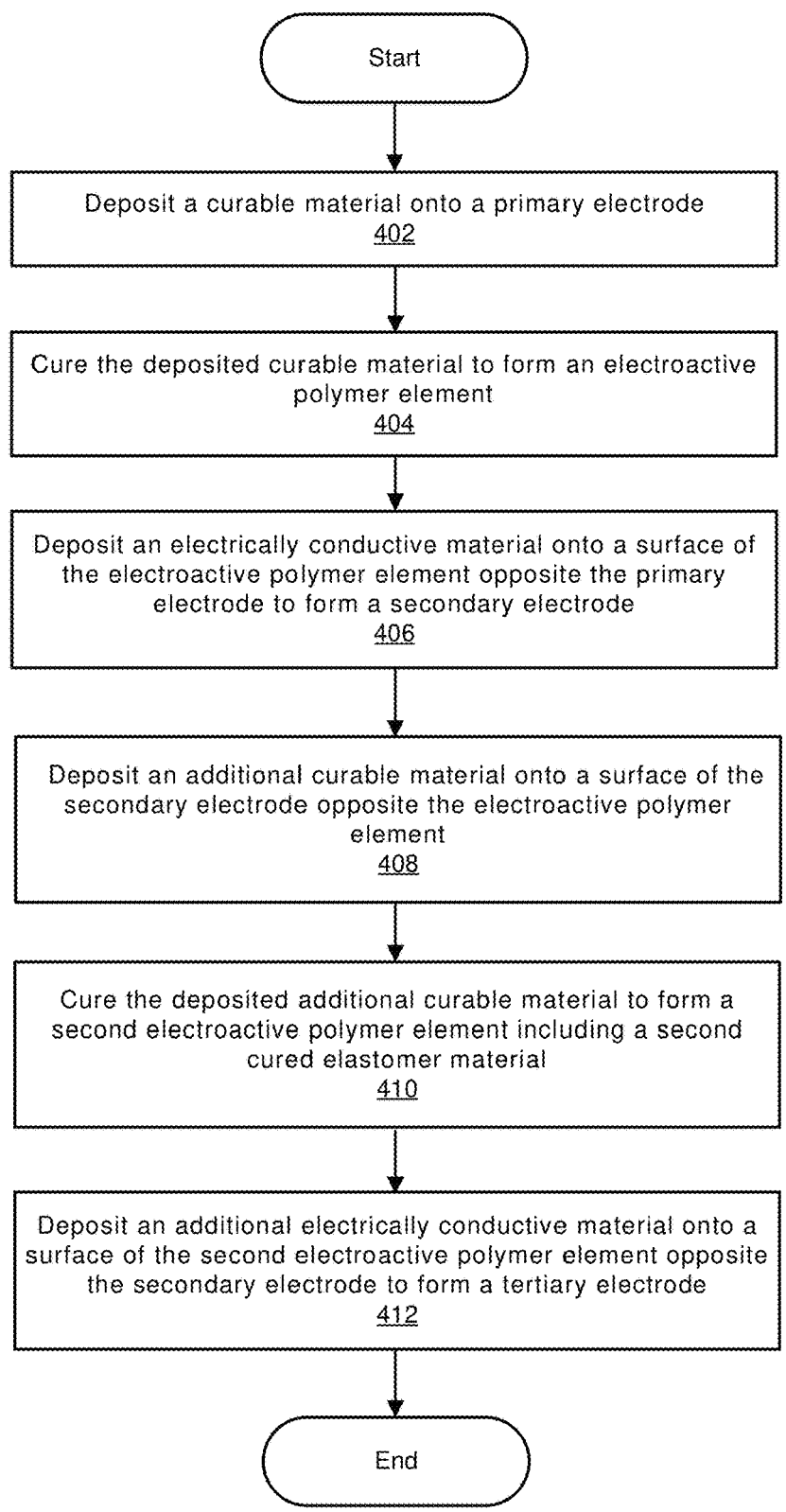
FIG. 4 shows flow diagram of an example method for the fabrication of one or more electroactive devices, in accordance with some embodiments of the disclosure.
Figure 6:
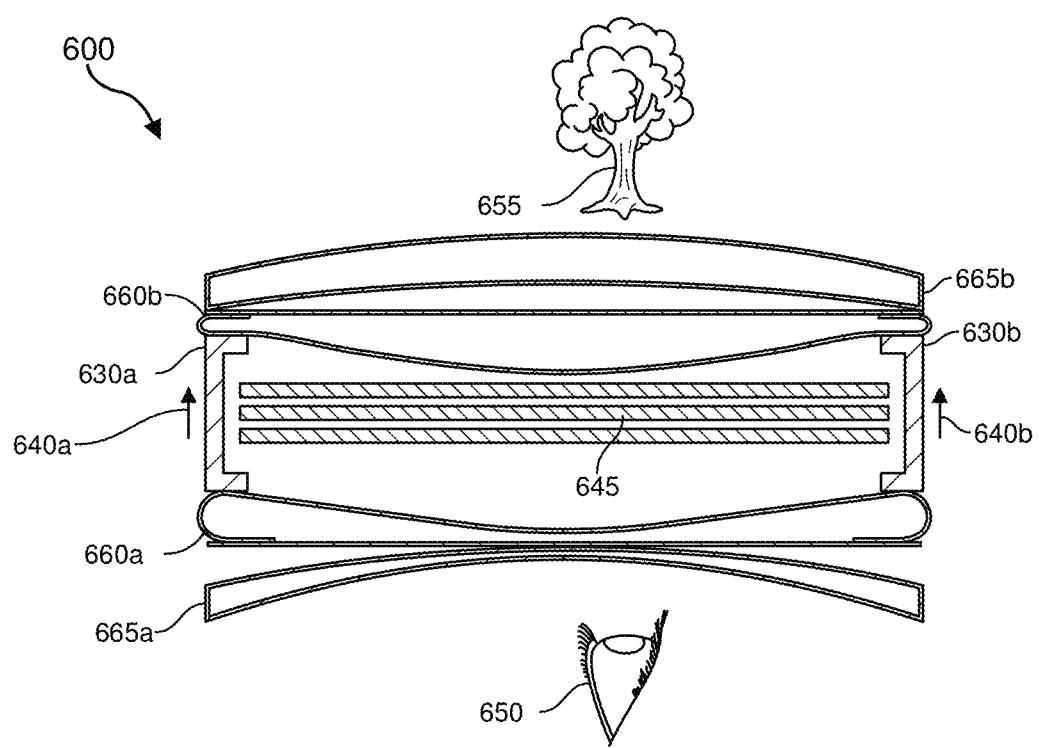
FIG. 6 shows a cross-sectional view of an example lens assembly device with multiple deformable elements (e.g., multiple liquid lenses) and which may include electroactive devices, in accordance with some embodiments of the disclosure.
Figure 7:
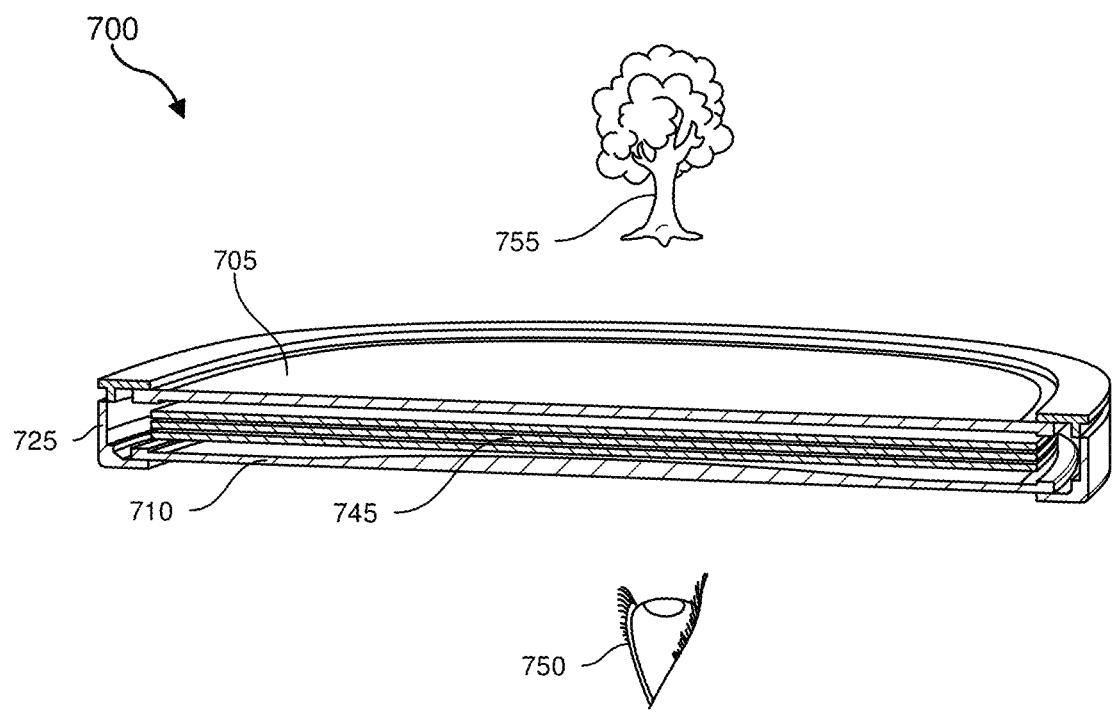
FIG. 7 shows another cross-sectional view of an example lens assembly device having multiple deformable elements and which may include electroactive devices, in accordance with some embodiments of the disclosure.
Figure 8:
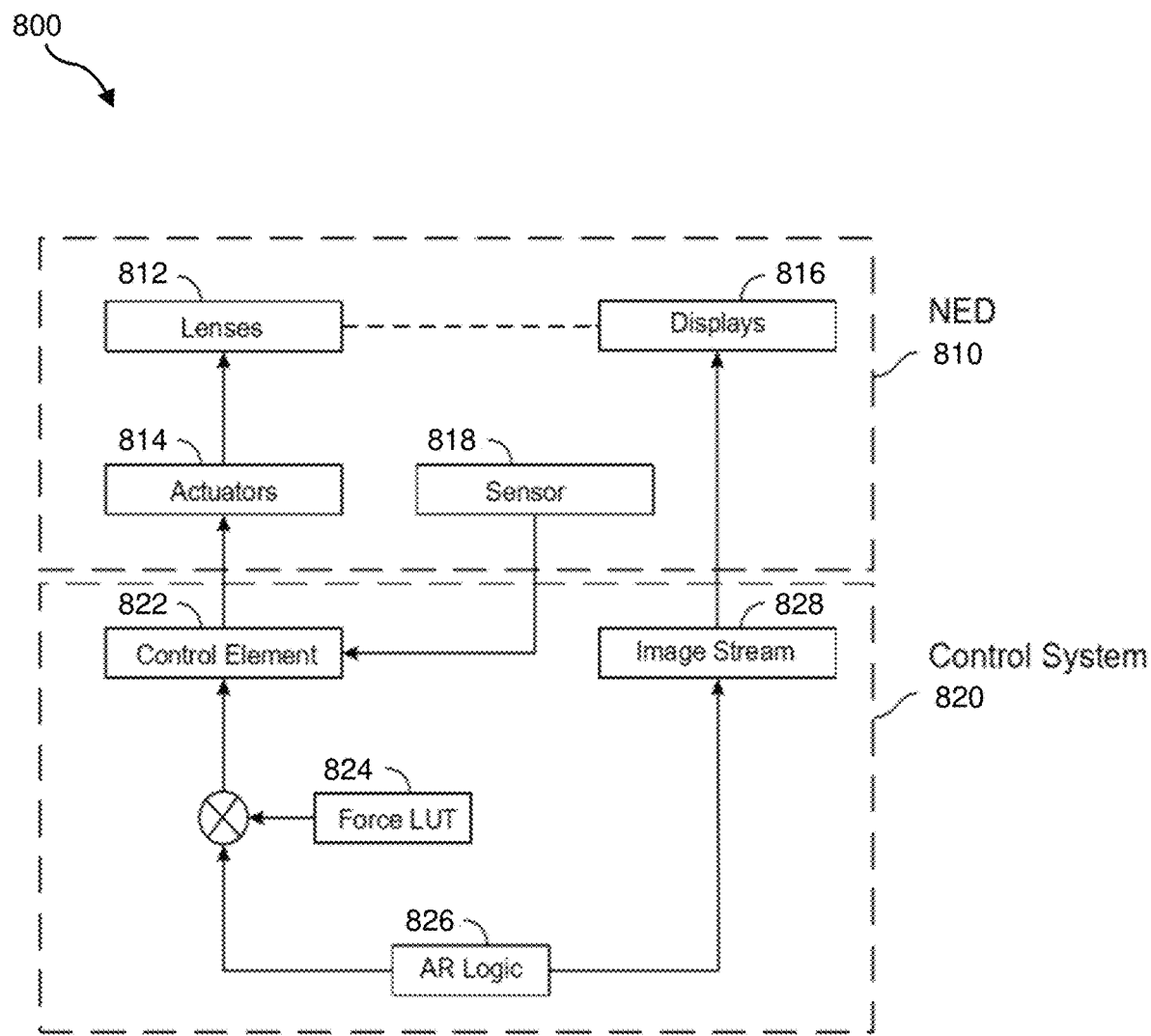
FIG. 8 shows a diagram of an example near-eye display system including a near-eye display and a control system, which may be communicatively coupled to each other, in accordance with some embodiments of the disclosure.
Figure 9:
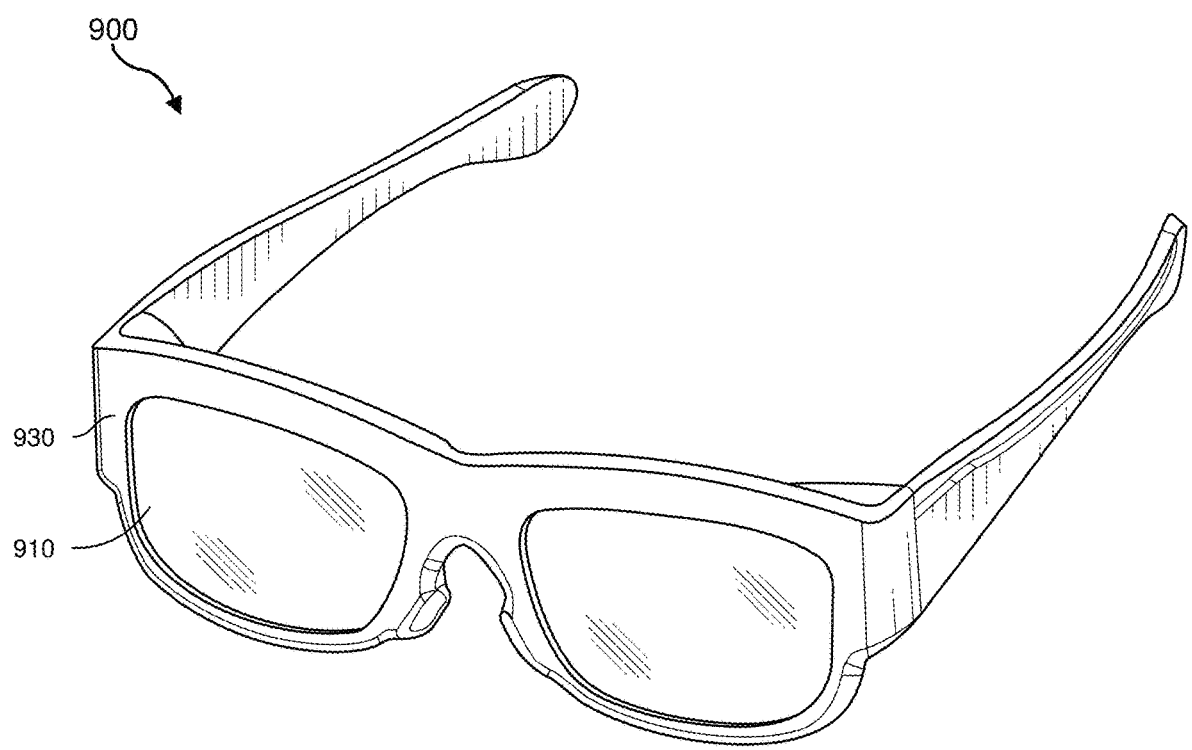
FIG. 9 shows a diagram of an example near-eye-display having lenses including a lens assembly with multiple liquid lenses, in accordance with some embodiments of the disclosure.

The following will provide, with reference to FIGS. 1A-9, detailed descriptions of systems, methods, and apparatuses for optical systems implementing electroactive devices (e.g., actuators). The discussion associated with FIG. 1A includes a description of an electroactive device that may be used with various embodiments. The discussion associated with FIGS. 1B and 1C includes a description of another electroactive device that may additionally or alternative be used with various embodiments. FIGS. 2-4 include descriptions of fabrication systems and methods that may be used to make the electroactive devices in accordance with various embodiments. The discussion relating to the embodiments depicted in FIGS. 5A and 5B includes descriptions of example deformable element (e.g., liquid lens) designs and devices incorporating the electroactive devices. The discussion relating to the embodiments depicted in FIGS. 6-7 includes lens assembly devices including the electroactive devices. The discussion relating to the embodiment depicted in FIG. 8 shows a diagram for a near-eye display and control system, in accordance with example embodiments of the disclosure. The discussion relating to the embodiment depicted in FIG. 9 shows an example near-eye-display having lenses that may be actuated with the electroactive devices. While many of the examples discussed herein may be directed to head-worn display systems, embodiments of the instant disclosure may be implemented in a variety of different types of devices and systems.

As noted, electroactive devices may include actuators that include electroactive polymers. In some embodiments, the electroactive devices may include at least two layers, with each layer being driven by a pair of electrodes. FIG. 1A shows an electroactive device (e.g., an actuator) 100 with a first electroactive polymer element (e.g., a first elastomer material) 105 and a second electroactive polymer element (e.g., a second elastomer material) 110, a primary electrode 130a, a secondary electrode 115, and a tertiary electrode 130b.

In some embodiments, the primary electrode 130a and the tertiary electrode 130b are optionally connected through a first contact (e.g., schoopage) layer 135 to a primary common electrode 140. In some examples, a secondary electrode 115 may be connected to a second optional contact (e.g., schoopage) layer 120 to a secondary common electrode 125. The secondary electrode 115 may be electrically isolated from the primary electrode 130a and tertiary electrode 130b, for example, with an insulator 145. The insulator 145 may be an electroactive polymer or a different dielectric material, such as, for example, an acrylate or silicone polymer. In some embodiments, the first contact layer 135 or the second contact layer 120 may include a metal (e.g., tin, aluminum, copper, gold, silver, and the like). In another aspect, the first contact layer 135 or the second contact layer 120 may include material that is similar, but not necessarily identical to, one or more of the electrodes (e.g., primary electrode 130a, secondary electrode 115, tertiary electrode 130b, primary common electrode 140, or secondary common electrode 125).

In some embodiments, the secondary electrode 115 may overlap (e.g., overlap in a horizontal direction) at least a portion of the primary electrode 130a, and a tertiary electrode 130b may overlap at least a portion of the secondary electrode 115. The first electroactive polymer element 105 may include a first elastomer material disposed between and abutting the primary electrode 130a and the secondary electrode 115. The second electroactive polymer element 110 may include a second elastomer material disposed between and abutting the secondary electrode 115 and the tertiary electrode 130b.

In some embodiments, the primary common electrode 140 may be electrically coupled (e.g., electrically contacted at an interface having a low contact resistance) to the primary electrode 130a and the tertiary electrode 130b. A secondary common electrode 125 may be electrically coupled to the secondary electrode 115. In some embodiments, the electroactive device may include additional layers that are not shown in FIG. 1A. For example, an additional electroactive polymer element (not shown) may be disposed on a side of the tertiary electrode 130b opposite the second electroactive polymer element 110. The additional electroactive polymer element may overlap the first electroactive polymer element 105 and the second electroactive polymer element 110. Moreover, an additional electrode may be disposed abutting a surface of one of the additional electroactive polymer element that faces away from the second electroactive polymer element 110. In some embodiments, the electroactive device may include more (e.g., two, three, or more) such additional electroactive polymer elements and corresponding electrodes (not shown). For example, an electroactive device may include a stack of from two electroactive polymer elements and corresponding electrodes to thousands of electroactive polymer elements (e.g., from 2 electroactive polymer elements to approximately 5, approximately 10, approximately 20, approximately 30, approximately 40, approximately 50, approximately 100, approximately 200, approximately 300, approximately 400, approximately 500, approximately 600, approximately 700, approximately 800, approximately 900, approximately 1000, approximately 2000, greater than approximately 2000 electroactive polymer elements).

In some embodiments, as used herein, an "elastomer material" may refer to a polymer with viscoelasticity (i.e., both viscosity and elasticity) and relatively weak intermolecular forces, and generally low elastic modulus (a measure of the stiffness of a solid material) and high failure strain compared with other materials. In some embodiments, the electroactive polymer elements (e.g., the first electroactive polymer element 105 and the second electroactive polymer element 110) may include an elastomer material that has an effective Poisson's ratio of less than approximately 0.35 (e.g., less than approximately 0.3, less than approximately 0.25, less than approximately 0.2, less than approximately 0.15, less than approximately 0.1, less than approximately 0.5). In at least one example, the elastomer material may have an effective density that is less than approximately 90% (e.g., less than approximately 80%, less than approximately 70%, less than approximately 60%, less than approximately 50%, less than approximately 40%) of the elastomer when densified (e.g., when the elastomer is compressed, for example, by electrodes to make the elastomer more dense).

In some example, the electroactive polymer elements (e.g., the first electroactive polymer element 105 and the second electroactive polymer element 110) may be voided and/or nanovoided (e.g., having a plurality of voids and/or nano-sized voids in the material composing the electroactive polymer elements). In some embodiments, the nanovoids may occupy at least approximately 10% (e.g., approximately 10% by volume, approximately 20% by volume, approximately 30% by volume, approximately 40% by volume, approximately 50% by volume, approximately 60% by volume, approximately 70% by volume, approximately 80% by volume, approximately 90% by volume) of the volume of the electroactive polymer elements. The voids and/or nanovoids may be either closed- or open-celled, or a mixture thereof. If they are open-celled, the void size may be the minimum average diameter of the cell. In some embodiments, the polymer layer may include a thermoset material and/or any other suitable material having an elastic modulus of less than approximately 10 GPa (e.g., approximately 0.5 GPa, approximately 1 GPa, approximately 2 GPa, approximately 3 GPa, approximately 4 GPa, approximately 5 GPa, approximately 6 GPa, approximately 7 GPa, approximately 8 GPa, approximately 9 GPa).

The voids and/or nanovoids may be any suitable size and, in some embodiments, the voids may approach the scale of the thickness of the polymer layer in the undeformed state. For example, the voids may be between approximately 10 nm to about equal to the gap between the paired two electrodes. In some embodiments, the voids may be between approximately 10 nm and approximately 1000 nm, such as between approximately 10 and approximately 200 nm (e.g., approximately 10 nm, approximately 20 nm, approximately 30 nm, approximately 40 nm, approximately 50 nm, approximately 60 nm, approximately 70 nm, approximately 80 nm, approximately 90 nm, approximately 100 nm, approximately 110 nm, approximately 120 nm, approximately 130 nm, approximately 140 nm, approximately 150 nm, approximately 160 nm, approximately 170 nm, approximately 180 nm, approximately 190 nm, approximately 200 nm, approximately 250 nm, approximately 300 nm, approximately 400 nm, approximately 500 nm, approximately 600 nm, approximately 700 nm, approximately 800 nm, approximately 900 nm, approximately 1000 nm).

In some examples, the term "effective density," as used herein, may refer to a parameter that may be obtained using a test method where a uniformly thick layer of the elastomer may be placed between two flat and rigid circular plates. In some embodiments, the diameter of the elastomer material being compressed may be at least 100 times the thickness the elastomer material. The diameter of the elastomer material may be measured, then the plates may be pressed together to exert a pressure of at least approximately $1 \times 10^6$ Pa on the elastomer, and the diameter of the elastomer is remeasured. The effective density may be determined from the following expression: $D_{ratio} = D_{uncompressed}/D_{compressed}$, where $D_{ratio}$ may represent the effective density ratio, $D_{uncompressed}$ may represent the density of the uncompressed polymer, and $D_{compressed}$ may represent the density of the uncompressed polymer.

In other embodiments, the first electroactive polymer element 105 may be deformable from an initial state to a deformed state when a first voltage is applied between the primary electrode 130a and the secondary electrode 115. Moreover, the second electroactive polymer element 110 may be deformable, in conjunction with deformation of the first electroactive polymer element 105, from an initial state to a deformed state when a second voltage is applied between the secondary electrode 115 and the tertiary electrode 130b. In some embodiments, applying the voltage to the electrodes (e.g., the primary electrode 130a, the secondary electrode 115, and/or the tertiary electrode 130b) may create at least an approximately 10% strain (e.g., an amount of deformation in the direction of the applied force resulting from the applied voltage divided by the initial dimension of the material) in the electroactive polymer element (e.g., the first electroactive polymer element 105 or second electroactive polymer element 110) in at least one direction (e.g., an x, y, or z direction with respect to a defined coordinate system).

In some embodiments, the application of a voltage to the electroactive polymer element (e.g., the first electroactive polymer element 105 or second electroactive polymer element 110) may change the internal pressure of gasses in the nanovoided regions of the electroactive polymer element. For example, gasses may diffuse either into or out of the electroactive polymer element during dimensional changes associated with its deformation. Such changes in the electroactive polymer elements can affect, for example, the hysteresis of an electroactive device (e.g., electroactive device 100) incorporating the electroactive polymer during dimensional changes, and also may result in drift when the electroactive polymer element's dimensions are rapidly changed. Accordingly, in an embodiment, the nanovoids may be filled with a gas to suppress electrical breakdown of the electroactive polymer element (for example, during deformation). In another aspect, the gas may include sulfur hexafluoride and/or any suitable gas. In another aspect, the electroactive device (e.g., an actuator) 100 may have a sealing layer (not shown) applied to the edges of the electroactive device 100, and/or to one or more of the electrodes (e.g., the primary electrode 130a, the secondary electrode 115, and/or the tertiary electrode 130b), or a combination thereof. Suitable sealing layers may include thin film layers of an inorganic material, such as silica, applied with any suitable method, including, for example, atomic layer deposition (ALD), physical vapor deposition (PVD), chemical vapor deposition (CVD), or the like. The thin film layers may also be made from one or more dyads of a polymer layer and an inorganic layer. In an embodiment, the sealing layer may also include a barrier material, such as polychlorotrifluoroethylene (PCTFE) and/or other polymer, applied by solvent and/or with initiated-CVD.

In some embodiments, the first electroactive polymer element 105 may have a maximum thickness in an undeformed state and a compressed thickness in the deformed state. The second electroactive polymer element 110 may have a maximum thickness in an undeformed state and a compressed thickness in the deformed state. In particular, the first elastomer material may have a density, when the first electroactive polymer element 105 is in the undeformed state, that is approximately 90% or less of a density of the first elastomer material when the first electroactive polymer element 105 is in the deformed state. Moreover, the second elastomer material may have a density, when the second electroactive polymer element 110 is in the undeformed state, that is approximately 90% or less of a density of the second elastomer material when the second electroactive polymer element 110 is in the deformed state. In some embodiments, the first elastomer material may exhibit a compressive strain of at least approximately 10% when a voltage is applied between the primary electrode 130a and the secondary electrode 115, and the second elastomer material 110 may exhibit a strain of at least approximately 10% when a voltage is applied between the secondary electrode 115 and the tertiary electrode 130b.

In some embodiments, the first electroactive polymer element 105 or the second electroactive polymer element 110 may include a first elastomer material and a second elastomer material, respectively, each having a Poisson's ratio of approximately 0.35 or less. In some embodiments, the first electroactive polymer element 105 or the second electroactive polymer element 110 may include particles of a material having a high dielectric constant, the particles having an average diameter between approximately 10 nm and approximately 1000 nm. In some embodiments, the material having the high dielectric constant may include barium titanate $BaTiO_3$), which is a member of the perovskite family and which may also include other titanates. Additionally or alternatively, any other suitable component may be added to the electroactive polymer material. $BaTiO_3$ is a ferroelectric material with a relatively high dielectric constant (e.g., a value of between approximately 500 and approximately 7000) and polarization and may be used in various electroactive devices described herein. Besides large polarizability and permittivity, large strains may also be achievable with $BaTiO_3$. Pure $BaTiO_3$ is an insulator whereas upon doping it may transform into a semiconductor in conjunction with the polymer material. In some embodiments, the particles of the materials having high dielectric constant may be included in the polymer to modify a mechanical (e.g., a Poisson's ratio) or electrical property (resistance, capacitance, etc.) of the first electroactive polymer element 105 or the second electroactive polymer element 110. In some embodiments, the first electroactive polymer element 105, the second electroactive polymer element 110, and/or the at least one additional electroactive polymer element (not shown) may have a thickness of approximately 10 nm to approximately 10 µm (e.g., approximately 10 nm, approximately 20 nm, approximately 30 nm, approximately 40 nm, approximately 50 nm, approximately 60 nm, approximately 70 nm, approximately 80 nm, approximately 90 nm, approximately 100 nm, approximately 200 nm, approximately 300 nm, approximately 400 nm, approximately 500 nm, approximately 600 nm, approximately 700 nm, approximately 800 nm, approximately 900 nm, approximately 1 µm, approximately 2 µm, approximately 3 µm, approximately 4 µm, approximately 5 µm, approximately 6 µm, approximately 7 µm, approximately 8 µm, approximately 9 µm, approximately 10 µm), with an example thickness of approximately 200 nm to approximately 500 nm.

In some embodiments, the first electroactive polymer element 105 and the second electroactive polymer element 110 may include a first elastomer material and a second elastomer material, respectively, each having a Poisson's ratio of approximately 0.35 or less. In some embodiments, the first electroactive polymer element 105 and/or the second electroactive polymer element 110 may include particles of a material to assist the formation or to support the voided regions, or both. Suitable particles include a silicate, such as silica, including structures resulting from silica gels, fumed silica, a titanate, such as barium titanate, a metal oxide, such as titanium dioxide, composites thereof, and the like. The particles may have an average diameter between approximately 10 nm and approximately 1000 nm, and the particles may form branched or networked particles with average dimensions of between approximately 100 and approximately 10,000 nm.

In some embodiments, the common electrodes (e.g., the primary common electrode 140 and the secondary common electrode 125) may be structured in a number of different ways than shown in FIG. 1A. For example, the common electrodes may form a sloped shape, or may be a more complex shape (e.g., patterned or freeform). In some embodiments, the common electrodes may be shaped to allow compression and expansion of the electroactive device during operation.

In some embodiments, the electrodes (e.g., the primary electrode 130a, the secondary electrode 115, the tertiary electrode 130b, the primary common electrode 140, and the secondary common electrode 125) may include metals such as aluminum, gold, silver, tin, copper, indium, gallium, zinc, and the like. Other conductive materials may be used, including carbon nanotubes, graphene, transparent conductive oxides (TCOs, e.g., indium tin oxide (ITO), zinc oxide (ZnO), etc.), and the like.

In some configurations, it may be necessary for the electrodes to stretch elastically. In such embodiments, the electrodes may include TCOs, graphene, carbon nanotubes, and the like. In other embodiments, for example, embodiments where electroactive devices have electroactive polymer elements including nanovoided electroactive polymer materials, relatively rigid electrodes (e.g. electrodes including a metal such as aluminum) may be used.

In some embodiments, the electrodes (e.g., the primary electrode 130a, the secondary electrode 115, the tertiary electrode 130b, the primary common electrode 140, and the secondary common electrode 125) may have a thickness of approximately 1 nm to approximately 100 nm, with an example thickness of approximately 10 nm to approximately 50 nm. Some of the electrodes (e.g., the primary electrode 130a, the secondary electrode 115, the tertiary electrode 130b, or the at least one additional electrode, not shown) may be designed to allow healing of electrical breakdown (e.g., the electric breakdown of elastomeric polymer materials) of the first electroactive polymer element 105, the second electroactive polymer element 110, and/or the at least one additional electroactive polymer element (not shown). In some embodiments, a thickness of an electrode (e.g., the primary electrode 130a, the secondary electrode 115, the tertiary electrode 130b, or the at least one additional electrode, not shown) that includes a self-healing electrode (e.g., an aluminum electrode) may be approximately 20 nm.

In some embodiments, the electrodes (e.g., the primary electrode 130a, the secondary electrode 115, the tertiary electrode 130b, the primary common electrode 140, and the secondary common electrode 125) may be fabricated using any suitable process. For example, the electrodes may be fabricated using physical vapor deposition (PVD), chemical vapor deposition (CVD), sputtering, spray-coating, spin-coating, atomic layer deposition (ALD), and the like. In another aspect, the electrodes may be manufactured using a thermal evaporator, a sputtering system, a spray coater, a spin-coater, an ALD unit, and the like.

According to some embodiments, as shown in FIGS. 1B and 1C, an electroactive device 150 may include a pair of electrodes including a primary electrode 152 and a secondary electrode 154. These paired electrodes may be spaced with an electroactive polymer element 156 formed of an electroactive nanovoided polymer positioned therebetween such that primary electrode 152 abuts a first surface 158 of nanovoided electroactive polymer element 156 and secondary electrode 154 abuts a second surface 160 of nanovoided electroactive polymer element 156 opposite the first surface. Electroactive polymer element 156 may additionally or alternatively have any suitable dimensions, including any suitable thickness and/or width, without limitation.

In some embodiments, electroactive polymer element 156 may be deformable from an undeformed state, as illustrated in FIG. 1B, or a partially deformed state to a more fully deformed state, as illustrated in FIG. 1C, when a voltage difference is applied between primary electrode 152 and secondary electrode 154. In some embodiments, the deformed state of electroactive polymer element 156 may be a compressed state in which electroactive polymer element 156 has a decreased thickness $T_2$ in the Y-direction, as shown in FIG. 1C. Thickness, as used herein, may refer to the extent of at least a portion of an electroactive polymer element parallel to an E-field generated between paired electrodes abutting the electroactive polymer element. In some embodiments, the initial state of electroactive polymer element 156 may be a state that is not influenced by an E-field or one already influenced by an E-field generated between primary electrode 152 and secondary electrode 154, and the E-field may be increased to amplify the E-field-induced deformations.

An exemplary direction $E_1$ of the lines of the electrostatic field between primary electrode 152 and secondary electrode 154 is represented in FIGS. 1B and 1C. According to some embodiments, an amount of deformation of electroactive polymer element 156 in the deformed state, as shown in FIGS. 1B and 1C, may correspond to the strength of the E-field or, equivalently, an amount of voltage applied between primary electrode 152 and secondary electrode 154. In at least one example, when electroactive polymer element 156 is in a compressed state, electroactive polymer element 156 may expand laterally (i.e., in the X-direction shown in FIG. 1B) such that electroactive polymer element 156 has an increased width in the X-direction. In some embodiments, electroactive polymer element 156 may be initially stretched in the X-direction.

Electroactive polymer element 156 may have a maximum thickness (e.g., thickness $T_1$ shown in FIG. 1B) in an undeformed or relaxed state and a minimum thickness (e.g., thickness $T_2$ shown in FIG. 1C) in a deformed state (e.g., a maximally deformed state) when a voltage difference of at least a certain value is applied between primary electrode 152 and secondary electrode 154. In some embodiments the maximum thickness of electroactive polymer element 156 may be from approximately 10 nm to approximately 10 μm. Additionally, or alternatively, a width of electroactive polymer element 156 in the undeformed state may be from approximately 100 nm to approximately 100 μm (e.g., approximately 100 nm, approximately 500 nm, approximately 1 μm, approximately 10 μm, approximately 20 μm, approximately 30 μm, approximately 40 μm, approximately 50 μm, approximately 60 μm, approximately 70 μm, approximately 80 μm, approximately 90 μm, approximately 100 μm). Width, as used herein, may refer to the extent of at least a portion of an electroactive polymer element in a dimension transverse to that of the expected electrostatic field.

FIG. 2 shows a diagram of an example apparatus for the fabrication of an electroactive device, in accordance with example embodiments of the disclosure. In particular, an apparatus 200 may be used to make an electroactive device (e.g., an actuator), such as electroactive device 100 in FIG. 1A and/or electroactive device 150 in FIGS. 1B and 1C. The apparatus 200 may use masks (e.g., shadow masks) to control the patterns of deposited materials to form the electroactive device. In some embodiments, the electroactive device may be fabricated on a surface 210 enclosed by a chamber 205, which may be evacuated (e.g., using one or more mechanical vacuum pumps to a predetermined level such as $10^{-6}$ Torr or below). The chamber 205 may include a rigid material (e.g., steel, aluminum, brass, glass, acrylic, and the like). FIG. 2 shows an embodiment where the surface 210 may include a rotating drum. In some embodiments, the rotation may generate centrifugal energy and cause the deposited material to spread more uniformly over any underlying sequentially deposited materials (e.g., electrodes, polymer elements, and the like) that are mechanically coupled to surface 210. Alternatively, the surface 210 may be fixed and the deposition and curing systems (e.g., monomer 220, vaporizer 225, electrode source 215, and/or source of radiation 230, as will be discussed in greater detail below) may be moving, or both the surface 210 and the deposition and curing systems may be moving simultaneously.

As will be elaborated on below, a method of making an electroactive device (e.g., an actuator similar to the electroactive device shown and described in connection with FIGS. 1A-1C) using the apparatus 200 may include (1) providing an electrically conductive layer (e.g., an electrode similar to primary electrode 130a in FIG. 1A or primary electrode 152 in FIGS. 1B and 1C) having a first surface, (2) depositing (e.g., vapor depositing) a monomer onto the electrode, (3) curing the monomer to form an electroactive polymer (e.g., similar to first electroactive polymer element 105 in FIG. 1A or electroactive polymer element 156 in FIGS. 1B and 1C), and (4) depositing another electrically conductive layer (e.g., an electrode similar to secondary electrode 115 in FIG. 1A or secondary electrode 154 in FIGS. 1B and 1C) onto the electroactive polymer. In some embodiments, the method may further include repeating one or more of the above to fabricate additional layers (e.g., second electroactive polymer element 110, tertiary electrode 130b, etc.) of the electroactive device, which may have a stacked configuration as shown in FIG. 1A.

In particular, in some embodiments, an electroactive device may be fabricated by first depositing a primary electrode 130a (see, e.g., FIG. 1A). Further, a curable material (e.g., a monomer) 220 may be deposited (e.g., vaporized by a vaporizer 225) onto the primary electrode 130a. In some embodiments, an inlet (not shown) to the chamber 205 may open and may input a corresponding monomer initiator for starting a chemical reaction. In some examples, "monomer," as used herein, may refer to a monomer that forms a given polymer (i.e., as part of an electroactive polymer element).

Moreover, the deposited curable material 220 may be cured with a source of radiation 230 (e.g., actinic energy) to form an electroactive polymer element (e.g., a primary electroactive polymer element 105 as shown in FIG. 1A) that includes a cured elastomer material. In some embodiments, the source of radiation 230 may, for example, include an energized array of filaments that may generate actinic energy to initiate reaction between the monomer and the monomer initiator to effect polymerization of the monomer. The monomer and monomer initiator may react upon exposure to radiation from radiation source 230 to form an electroactive polymer element (e.g., primary electroactive polymer element 105). In some examples, "actinic energy," as used herein, may refer to energy capable of breaking covalent bonds in a material. Examples may include electrons, electron beams, x-rays, gamma rays, ultraviolet and visible light at appropriately high energy levels, and ions. In some embodiments, the cured elastomer material may include at least one non-polymeric component in a plurality of defined regions and the method may further include removing at least a portion of the at least one non-polymeric component from the cured elastomer material to form a nanovoided polymer material (to be discussed further in connection with FIG. 3, below).

An electrically conductive material may then be deposited onto a surface of the primary electroactive polymer element 105 opposite the primary electrode 130a to form a secondary electrode 115 (see FIG. 1A). Moreover, an additional curable material may be deposited onto a surface of the secondary electrode 115 opposite the primary electroactive polymer element 105. For example, the deposited additional curable material may be cured to form a second electroactive polymer element 110, as shown in FIG. 1A, including a second cured elastomer material. In some embodiments, an additional electrically conductive material may be deposited onto a surface of the second electroactive polymer element 110 opposite the secondary electrode 115 to form a tertiary electrode 130b, as shown in FIG. 1A.

In some embodiments, an exhaust port (not shown) of the chamber 205 may open to release at least a portion of the vapor in chamber 205 during and/or between one or more depositions of the materials (e.g., monomers, monomers, monomer initiators, conductive materials, etc.). In another embodiment, chamber 205 may be purged (e.g., with a gas or the application of a vacuum, or both), to remove a portion of the vapor (e.g., monomers, monomer initiators, metal particles, and any resultant biproducts). Thereafter one or more of the previous steps may be repeated (e.g., for a second electroactive polymer element 110, etc.), as described above. In this way, individual layers of the electroactive device 100 may be maintained at high purity levels.

In some embodiments, the deposition of the materials (e.g., monomers, monomers, monomer initiators, conductive materials, etc.) of the electroactive device may be performed using a deposition process, such as chemical vapor deposition (CVD), to be described further below. CVD may refer to a vacuum deposition method used to produce high-quality, high-performance, solid materials. In CVD, a substrate may be exposed to one or more precursors, which may react and/or decompose on the substrate surface to produce the desired deposit (e.g., one or more electrodes, electroactive polymers, etc.). Frequently, volatile by-products are also produced, which may be removed by gas flow through the chamber 205.

In some embodiments, the apparatus 200 may apply an atmospheric pressure CVD (APCVD) coating formation technique (e.g., CVD at atmospheric pressure). In another aspect, the apparatus 300 may apply a low-pressure CVD (LPCVD) process (e.g., CVD at sub-atmospheric pressures). In some embodiments, LPCVD may make use of reduced pressures that may reduce unwanted gas-phase reactions and improve the deposited material's uniformity across the substrate. In one aspect, the apparatus 300 may apply an ultrahigh vacuum CVD (UHVCVD) process (e.g., CVD at very low pressure, typically below approximately $10^{-6}$ Pa (equivalently, approximately $10^{-8}$ torr)).

In some embodiments, the apparatus 200 may apply an aerosol assisted CVD (AACVD) process (e.g., a CVD in which the precursors are transported to the electroactive device) by means of a liquid/gas aerosol, which may be generated ultrasonically or with electrospray. In some embodiments, AACVD may be used with non-volatile precursors.

In some embodiments, the apparatus 200 may apply a direct liquid injection CVD (DLICVD) process (e.g., a CVD in which the precursors are in liquid form, for example, a liquid or solid dissolved in a solvent). Liquid solutions may be injected in the chamber 205 towards one or more injectors. The precursor vapors may then be transported to the electroactive device as in CVD. DLICVD may be used on liquid or solid precursors, and high growth rates for the deposited materials may be reached using this technique.

In some embodiments, the apparatus 200 may apply a hot wall CVD process (e.g., CVD in which the chamber 205 is heated by an external power source and the electroactive device is heated by radiation from the heated wall of the chamber 205). In another aspect, the apparatus 200 may apply a cold wall CVD process (e.g., a CVD in which only the electroactive device is directly heated, for example, by induction, while the walls of the chamber 205 are maintained at room temperature).

In some embodiments, the apparatus 200 may apply a microwave plasma-assisted CVD (MPCVD) process, where microwaves are used to enhance chemical reaction rates of the precursors. In another aspect, the apparatus 200 may apply a plasma-enhanced CVD (PECVD) process (e.g., CVD that uses plasma to enhance chemical reaction rates of the precursors). In some embodiments, PECVD processing may allow deposition of materials at lower temperatures, which may be useful in withstanding damage to the electroactive device or in depositing certain materials (e.g., organic materials and/or some polymers).

In some embodiments, the apparatus 200 may apply a remote plasma-enhanced CVD (RPECVD) process. In some embodiments, RPECVD may be similar to PECVD except that the electroactive device may not be directly in the plasma discharge region. In some embodiments, the removal of the electroactive device from the plasma region may allow for the reduction of processing temperatures down to room temperature.

In some embodiments, the apparatus 200 may apply an atomic-layer CVD (ALCVD) process. In some embodiments, ALCVD may deposit successive layers of different substances to produce layered, crystalline film coatings on the electroactive device.

In some embodiments, the apparatus 200 may apply a combustion chemical vapor deposition (CCVD) process. In some embodiments, CCVD (also referred to as flame pyrolysis) may refer to an open-atmosphere, flame-based technique for depositing high-quality thin films (e.g., layers of material ranging from fractions of a nanometer (monolayer) to several micrometers in thickness) and nanomaterials, which may be used in forming the electroactive device.

In some embodiments, the apparatus 200 may apply a hot filament CVD (HFCVD) process, which may also be referred to as catalytic CVD (cat-CVD) or initiated CVD (iCVD), as noted above. In some embodiments, this process may use a hot filament to chemically decompose the source gases to form the materials of the electroactive device. Moreover, the filament temperature and temperature of portions of the electroactive device may be independently controlled, allowing colder temperatures for better adsorption rates at the electroactive device, and higher temperatures necessary for decomposition of precursors to free radicals at the filament.

In some embodiments, the apparatus 200 may apply a hybrid physical-chemical vapor deposition (HPCVD) process. HPCVD may involve both chemical decomposition of precursor gas and vaporization of a solid source to form the materials on the electroactive device.

In some embodiments, the apparatus 200 may apply metalorganic chemical vapor deposition (MOCVD) process (e.g., a CVD that uses metalorganic precursors) to form materials on the electroactive device.

In some embodiments, the apparatus 200 may apply a rapid thermal CVD (RTCVD) process. This CVD process uses heating lamps or other methods to rapidly heat the electroactive device. Heating only the electroactive device rather than the precursors or chamber walls may reduce unwanted gas-phase reactions that may lead to particle formation in the electroactive device.

In some embodiments, the apparatus 200 may apply a photo-initiated CVD (PICVD) process. This process may use UV light to stimulate chemical reactions in the precursor materials used to make the materials for the electroactive device. Under certain conditions, PICVD may be operated at or near atmospheric pressure.

In some embodiments, as will be elaborated on below, a method of making electroactive devices including nanovoided polymers may include (1) depositing a curable material (e.g., a monomer such as an acrylate or a silicone) and a solvent for the curable material onto a substrate, (2) heating the curable material with at least a portion of the solvent remaining with the cured monomer, and (3) removing the solvent from the cured monomer. In particular, FIG. 3 shows another diagram of an example apparatus for the fabrication of an electroactive device (e.g., an actuator), in accordance with example embodiments of the disclosure. In particular, an apparatus 300 may be used for making the electroactive device having electroactive polymers with nanovoids. The apparatus 300 may be similar to the apparatus 200 shown in FIG. 2. However, a flowable material (e.g., a solvent) may be combined with the curable materials (e.g., monomers and conductive materials) to create a flowable mixture that may be used for producing electroactive polymers with nanovoids. The monomers may be monofunctional or polyfunctional, or mixtures thereof. Polyfunctional monomers may be used as crosslinking agents to add rigidity or to form elastomers. Polyfunctional monomers may include difunctional materials such as bisphenol fluorene (EO) diacrylate, trifunctional materials such as trimethylolpropane triacrylate (TMPTA), and/or higher functional materials. Other types of monomers may be used, including, for example, isocyanates, and these may be mixed with monomers with different curing mechanisms.

In some embodiments, the flowable material may be combined (e.g., mixed) with a curable material 320 (e.g., a monomer). In some embodiments, the curable material 320 itself may be combined with at least one non-curable component (e.g., particles of a material having a high dielectric constant) to form a mixture including the curable material 320 and the at least one non-curable component, for example, on an electrode (e.g., the primary electrode 130a or the secondary electrode 115 of FIG. 1A) of the electroactive device. Alternatively, the flowable material (e.g., solvent) may be introduced into the vaporizer 225 to deposit (e.g., via vaporization or, in alternative embodiments, via printing) the curable material 320 onto the electrode. In some embodiments, the flowable material (e.g., solvent) may be deposited as a separate layer either on top or below a curable material (e.g., a monomer) 320, and the solvent and curable material 320 may be allowed to diffuse into each other before being cured by the source of radiation 230 to generate an electroactive polymer having nanovoids. In some embodiments, after the curable material is cured, the solvent may be allowed to evaporate before another electroactive polymer or another electrode is formed. In some embodiments, the evaporation of the solvent may be accelerated by the application of heat to the surface 210 with a heater 325, which may, for example, by disposed within a drum forming surface 210 and/or any other suitable location, or by reducing the pressure of the solvent above the substrate using a cold trap 330 (e.g., a device that condenses vapors into a liquid or solid), or a combination thereof. Isolators (not shown) may be added to the apparatus 200 to prevent, for example, the solvent vapor from interfering with the radiation source 230 or the electrode source 215.

In some embodiments, the solvent may have a vapor pressure that is similar to at least one of the monomers being evaporated. The solvent may dissolve both the monomer 320 and the generated electroactive polymer, or the solvent may dissolve only the monomer 320. Alternatively, the solvent may have low solubility for the monomer 320, or plurality of monomers if there is a mixture of monomers being applied. Furthermore, the solvent may be immiscible with at least one of the monomers, and may at least partially phase separate when condensed on the substrate.

In some embodiments, there may be multiple vaporizers 225, with each of the multiple vaporizers applying a different material, including solvents, non-solvents, monomers, and/or ceramic precursors such as tetraethyl orthosilicate and water, and optionally a catalyst for forming a sol gel such as HCl or ammonia.

FIG. 4 shows a diagram of an example method 400 for the fabrication of one or more electroactive devices, in accordance with example embodiments of the disclosure. At block 402, a curable material (e.g., a monomer) may be deposited onto a primary electrode (e.g., primary electrode 130a in FIG. 1A or primary electrode 152 in FIGS. 1B and 1C). The deposition may occur in a dedicated apparatus (e.g., a CVD apparatus) including a chamber that is pumped down to a given vacuum level (e.g., less than $10^{-6}$ Torr). The monomer may serve as a precursor for an electroactive polymer element, and may be vaporized to form a monomer film on the primary electrode. The primary electrode may be deposited similarly (e.g., vaporized in the same apparatus) using similar means.

At block 404, the deposited curable material may be cured to form an electroactive polymer element (first electroactive polymer element 105 in FIG. 1A or electroactive polymer element 156 in FIGS. 1B and 1C) including a cured elastomer material. The deposited curable material may be cured with a source of radiation (e.g., actinic energy) to form an electroactive polymer element (e.g., a primary electroactive polymer element) that includes, for example, a cured elastomer material. In some embodiments, the deposited curable material may be cured during deposition (e.g., during vaporization) and/or after deposition onto the primary electrode.

At block 406, an electrically conductive material may be deposited onto a surface of the electroactive polymer element opposite the primary electrode to form a secondary electrode (e.g., secondary electrode 115 in FIG. 1A or secondary electrode 154 in FIGS. 1B and 1C). The electrically conductive material may include the same or different material than the primary electrode. In some embodiments, the work function of the primary and secondary electrodes may be substantially the same or different by a predetermined amount (e.g., approximately 1 electron-volt, eV).

In some embodiments, at block 408, an additional curable material (e.g., a monomer) may be deposited onto a surface of the secondary electrode opposite the electroactive polymer element. The monomer may, for example, serve as a precursor for an additional electroactive polymer element, and may be vaporized to form a monomer film on the secondary electrode.

At block 410, the deposited additional curable material may be cured to form a second electroactive polymer element (e.g., second electroactive polymer element 110 in FIG. 1A) including a second cured elastomer material. The deposited curable material may be cured with a source of radiation (e.g., actinic energy) to form an electroactive polymer element (e.g., a second electroactive polymer element) that includes, for example, a cured elastomer material. In some embodiments, the deposited curable material may be cured during deposition (e.g., during vaporization) and/or after deposition onto the secondary electrode.

At block 412, an additional electrically conductive material may be deposited onto a surface of the second electroactive polymer element opposite the secondary electrode to form a tertiary electrode (e.g., tertiary electrode 130b in FIG. 1A). The electrically conductive material may include the same or different material than the primary electrode or the secondary electrode. In some embodiments, the work function of the primary, secondary, and/or tertiary electrodes may be substantially the same or different by a predetermined amount.

In some aspects, another method of generating a nanovoided polymer for use in connection with an electroactive device (such as electroactive devices described variously herein) may include co-depositing (i) a monomer or mixture of monomers, (ii) a surfactant, and (iii) a nonsolvent material associated with the monomer(s) which is compatible with the surfactant. In various examples, the monomer(s) may include, but not be limited to, ethyl acrylate, butyl acrylate, octyl acylate, ethyethoxy ethyl acrylate, 2-chloroethyl vinyl ether, chloromethyl acrylate, methacrylic acid, allyl glycidyl ether, and/or N-methylol acrylamide. Other curing agents such as polyamines, higher fatty acids or their esters, and/or sulfur may be used as the monomer(s). In some aspects, the surfactant may be ionic or non-ionic (for example SPAN 80, available from Sigma-Aldrich Company). In another aspect, the non-solvent material may include organic and/or inorganic non-solvent materials. For instance, the non-solvent material may include water or a hydrocarbon or may include a highly polar organic compound such as ethylene glycol. As noted, the monomer or monomers, non-solvent, and surfactant may be co-deposited. Alternatively, the monomer or monomers, non-solvent, and/or surfactant may be deposited sequentially. In one aspect, a substrate temperature may be controlled to generate and control one or more properties of the resulting emulsion generated by co-depositing or sequentially depositing the monomer or monomers, non-solvent, and surfactant. The substrate may be treated to prevent destabilization of the emulsion. For example, an aluminum layer may be coated with a thin polymer layer made by depositing a monomer followed by curing the monomer.

Figure 5A:
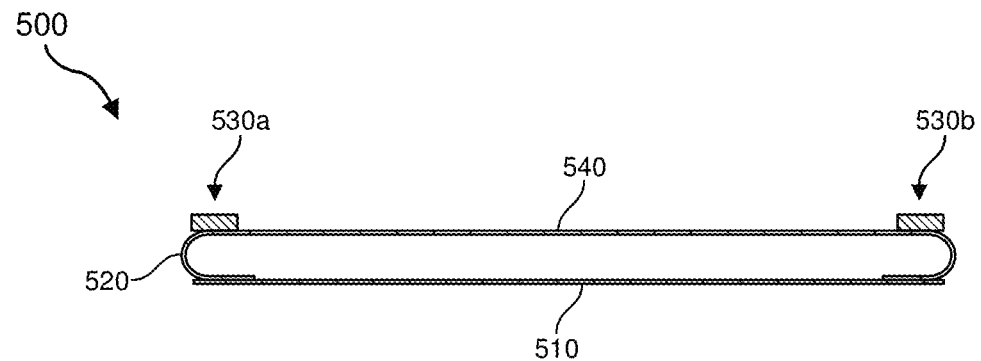
FIG. 5A shows a cross-sectional view of an example deformable element and a lens assembly and which may include electroactive devices, in accordance with some embodiments of the disclosure.

FIG. 5A shows a diagram of a cross-sectional view of an example deformable element and a lens assembly which may include on or more electroactive devices, in accordance with example embodiments of the disclosure. As shown in FIG. 5A, adjustable lens 500 may be an adjustable lens with a structural support element 510 (e.g., a rigid backplane) and a deformable optical element 540, with a seal 520 formed between the structural support element 510 and the deformable optical element 540. In various embodiments, the adjustable lens may include any suitable type of lens with adjustable optical properties (e.g., adjustable optical power/focal length, correcting for wavefront distortion and/or aberrations, etc.). In some examples, as will be explained in greater detail below, an adjustable lens may include a liquid lens. For example, adjustable lens 500 may be filled with an optical medium that is at least partially encapsulated by a deformable optical element (i.e., between structural support element 510 and deformable optical element 540). For example, lens 500 may be filled with a liquid or a semi-solid material (e.g., a gel, a semi-solid polymer, etc.). In general, lens 500 may contain a substantially transparent material that deforms and/or flows under pressure.

Structural support element 510 and deformable optical element 540 may be composed of any suitable materials. In some examples, structural support element 510 may include a rigid material. For example, structural support element 510 may be composed of a rigid, substantially transparent polymer. Deformable optical element 540 may include a substantially transparent and elastic material. For example, deformable optical element 540 may be composed of a natural or synthetic elastomer that returns to a resting state when a deforming force is removed. As will be explained in greater detail below, in some examples deformable optical element 540 may be deformed using an electroactive device generating a directly-driven force to produce a desired optical power or other optical property for lens 500.

Although the lens 500 is unactuated in FIG. 5A, forces may be applied by electroactive device(s) to lens 500 to actuate the lens 500 (as will be described in connection with FIG. 5B). Further, such forces may be uniform around a perimeter of lens 500 or may be variable around the perimeter of lens 500. For example, a vector (not shown) corresponding to a force applied by mechanical action of a first electroactive device (e.g., a first actuator) 530*a* may be the same as a vector corresponding to a force applied by mechanical action of a second electroactive device (e.g., a second actuator) 530*b*. Alternatively, a vector corresponding to a force applied by mechanical action of a first electroactive device 530*a* may be different from a vector corresponding to a force applied by mechanical action of a second electroactive device 530*b*.

Figure 5B:
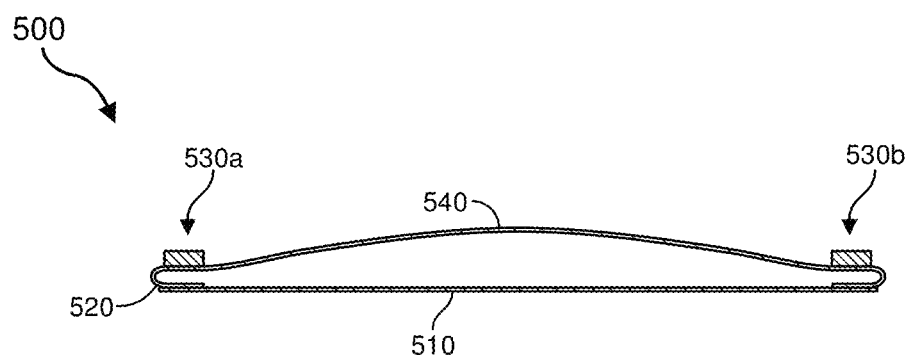
FIG. 5B shows another cross-sectional view of the deformable element and a lens assembly of FIG. 5A in an actuated state, in accordance with some embodiments of the disclosure.

FIG. 5B shows a diagram of a cross-sectional view of the example deformable element and a lens assembly of FIG. 5A in an actuated state, in accordance with example embodiments of the disclosure. In particular, FIG. 5B depicts adjustable lens 500 being actuated by receiving force applied by mechanical action of two different electroactive devices. In this example, a first electroactive device (e.g., a first actuator) 530*a* may apply a pushing force (not shown) having a vector of a first magnitude and first direction to a first area on the perimeter of lens 500. A second electroactive device (e.g., a second actuator) 530*b* may apply a pushing force (not shown) having vector of a second magnitude and second direction to a second area on the perimeter of lens 500 to achieve a desired optical power or other optical property for the lens 500. Those skilled in the art will understand that other embodiments may use various combinations of compression and distension, with various numbers of actuators applying varying forces to various locations on a deformable optical element to achieve desired optical properties for the lens.

The forces applied by the electroactive device in FIG. 5A to actuate the lens 500, as well as any other suitable forces, may be applied by any suitable type electroactive device, such as that shown and described in connection with FIGS. 1A-1C and 4 of the disclosure. In another aspect, at least one of the electroactive devices (e.g., one of the electroactive devices 530*a* and 530*b*) may include a direct-drive actuator. As used in some embodiments, the term "direct-drive actuator" may refer to any actuator used in a direct-drive system or configuration (e.g., any configuration that does not involve an intermediate, off-axis device to transmit power). In contrast, indirect-drive systems may have at least one drive-train component (e.g., a belt, a chain, a ball-screw mechanism, a gear, etc.) that is not connected along the same axis of movement as the actuator. Examples of direct-drive actuators may include, without limitation, electrically driven actuators, electroactive benders, voice coil actuators, shape memory alloys, hydraulic pumps, etc.

As noted, in various embodiments, a direct-drive actuator may include a bender. In some examples, the term "bender," as used herein, may refer, without limitation, to an electrically-driven actuator based on a plate or beam design that converts in-plane contraction, via an applied electric field, into out-of-plane displacement. A bender or bending actuator may include an all-electroactive or composite material stack operated in a bimorph, unimorph, or multilayered monolith configuration. In some embodiments, the term "unimorph bender," as used herein, may refer, without limitation, to a beam or plate having an electroactive layer and an inactive layer, in which displacement results from contraction or expansion of the electroactive layer. In some embodiments, the term "bimorph bender," as used herein, may refer, without limitation, to a beam or plate having two electroactive layers, in which displacement results from expansion or contraction of one layer with alternate contraction or expansion of the second layer.

In some embodiments, the term "multilayer bender," as used herein, may refer, without limitation, to a multilayer stack of electroactive, electrode, and insulation layers integrated with alternating contracting and expanding electroactive layers into a monolithic bender. The piezoelectric layers in multilayer piezoelectric benders may enable high electric fields (and therefore high force and displacement) to occur at low voltages. Multilayer benders may include multiple thin piezoceramic layers, which may require lower voltages to achieve similar internal stress to bimorph and unimorph designs. Charge and voltage control in open or closed loops may also be implemented in multilayer benders, with some adjustment. In some examples, a control system for a multilayer bender may not require a high voltage power supply.

According to some embodiments, an actuator may be a frame-contoured ring bender and/or may include stacked or overlapping benders. Furthermore, actuator volume may be constrained to an edge region outside an optical aperture, which may include a perimeter volume of a lens, an optical element, an optical sub-assembly, etc. As noted, electroactive device(s) such as an actuator (or a set of actuators) may provide equal or varied force and displacement at discrete points or along a spatially-defined distribution at the perimeter of a lens.

The electroactive device including direct-drive benders disclosed herein may include a electroactive polymer element that is disposed between two electrodes. In such examples, methods of forming an electroactive device may involve forming electrodes and an electroactive polymer simultaneously (e.g., via coflowing, slot die coating, etc.).

FIG. 6 shows a diagram of an example cross-sectional view of a lens assembly device with multiple deformable elements (e.g., multiple liquid lenses) including electroactive devices, in accordance with example embodiments of the disclosure. In particular, FIG. 6 shows a side view of a lens-display assembly 600. As shown in FIG. 6, lens-display assembly 600 may include an adjustable-focus lens 660(a) and an adjustable-focus lens 660(b). In addition, lens-display assembly 600 may include a carriage 630(a) and a carriage 630(b), each of which connect adjustable-focus lens 660(a) to adjustable-focus lens 660(b) (e.g., via respective electroactive devices).

Because carriages 630(a) and 630(b) are connected to electroactive devices (e.g., direct-drive actuators) coupled to both adjustable-focus lens 660(a) and adjustable-focus lens 660(b), when carriage 630(a) and/or 630(b) moves, carriage 630(a) and/or 630(b) may apply forces to adjustable-focus lens 660(a) and adjustable focus lens 660(b) simultaneously, thereby deforming and modifying the optical power of adjustable-focus lenses 660(a) and 660(b).

In addition, in some examples, lens-display assembly 600 may include a display 645 situated between adjustable-focus lenses 660(a) and 660(b). For example, display 645 may include an augmented-reality display that is substantially translucent (except for, e.g., virtual objects displayed by display 645), allowing a user's eye 650 to see beyond display 645 to real-world objects such as a tree 655 illustrated in FIG. 6.

In some embodiments, carriages 630(a) and 630(b) may each apply equal pressure to adjustable-focus lens 660(a) and adjustable focus lens 660(b) (e.g., pressure sufficient to maintain tension within the respective membranes of adjustable-focus lenses 660(a) and 660(b) but not to deform adjustable-focus lenses 660(a) and 660(b)). Accordingly, adjustable-focus lenses 660(a) and 660(b) may be flat and exhibit no substantial optical power. Thus, the apparent accommodation distance of a virtual object displayed by display 645 may be the actual distance of display 645 from the user's eye 650. Likewise, lens-display assembly 600 may not significantly change the appearance of tree 655 to the user's eye 650.

In some examples, one or more of the carriages described herein may be rigid. Additionally or alternatively, one or more of the carriages described herein may have a degree of elasticity in one or more directions. In some examples, the length of the carriages may be fixed. In some examples, the length of the carriages may be adjustable. For example, the length of a carriage may be manually adjustable by using, e.g., a set screw or an adjustable threaded shaft. Additionally or alternatively, the length of the carriage may be dynamically adjustable through the use of, e.g., a piezoelectric stack.

FIG. 6 depicts lens-display assembly 600 in an adjusted state. As shown in FIG. 6, carriages 630(a) and 630(b) may be actuated by one or more actuators (e.g., electroactive devices as described herein) to move away from the user's eye 650 and adjustable-focus lens 660(a), and toward adjustable-focus lens 660(b). In the process, forces 640(a) and 640(b) applied by carriages 630(a) and 630(b), respectively, may shape adjustable-focus lens 660(a) into a plano-concave lens, and shape adjustable-focus lens 660(b) into a plano-convex lens. Adjustable-focus lens 660(a) may thereby cause an image displayed by display 645 to appear closer to eye 650. At the same time, adjustable-focus lens 660(b) may compensate for the optical power created by adjustable-focus lens 660(a) so that the appearance of tree 655 is not significantly affected by the change to adjustable-focus lens 660(a).

As should be appreciated, in some examples intermediate positions of carriages 630(a) and 630(b) may result in intermediate changes to the apparent accommodation distance of images displayed by display 645, allowing for a continuous range of possible apparent accommodation distances for virtual objects while maintaining the fidelity of the appearance of real-world objects.

In some embodiments, additional optical elements such as lens 665a and lens 665b may be included to provide additional optical power. In some embodiments, the lenses 665a and 665b may include prescription lenses that may be used to treat refractive errors of the eye, which may include, for example, myopia, hypermetropia, astigmatism, and presbyopia, and the like. In other embodiments, the prescription lenses may be customized to correct for a given user's refractive errors, which may include various components, such as a sphere component to address myopia and/or presbyopia, a cylinder component to address astigmatism, and a prism component to address strabismus and other binocular vision disorders.

FIG. 7 illustrates a cross-section of a lens-display assembly 700, in accordance with at least one embodiment. As shown in FIG. 7, lens-display assembly 700 may include an adjustable lens 705, an adjustable lens 710, a display 745 positioned between adjustable lenses 705 and 710, and a lens assembly housing 725. In some examples, the volume between lens assembly housing 725 and display 745 may provide space for electroactive devices (e.g., direct drive actuators) as described herein. According to some examples, the combination of adjustable lenses 705 and 710 may modify the apparent accommodation distance of images created by display 745 without changing the appearance of distant real-world objects (e.g., tree 755) as perceived by a user's eye.

As shown in FIG. 8, a near-eye display system 800 may include a near-eye display (NED) 810 and a control system 820, which may be communicatively coupled to each other. The near-eye display 810 may include lenses 812, electroactive devices 814, displays 816, and a sensor 818. Control system 820 may include a control element 822, a force lookup table 824, and augmented reality (AR) logic 826.

Augmented reality logic 826 may determine what virtual objects are to be displayed and real-world positions onto which the virtual objects are to be projected. Accordingly, augmented reality logic 826 may generate an image stream 828 that is displayed by displays 816 in such a way that alignment of right- and left-side images displayed in displays 816 results in ocular vergence toward a desired real-world position.

Control element 822 may use the same positioning information determined by augmented reality logic 826, in combination with force lookup table (LUT) 824, to determine an amount of force to be applied by electroactive devices 814 (e.g., actuators), as described herein, to lenses 812. Electroactive devices 814 may, responsive to control element 822, apply appropriate forces to lenses 812 to adjust the apparent accommodation distance of virtual images displayed in displays 816 to match the apparent vergence distance of the virtual images, thereby reducing or eliminating vergence-accommodation conflict. Control element 822 may be in communication with sensor 818, which may measure a state of the adjustable lens. Based on data received from sensor 818, the control element 822 may adjust electroactive devices 814 (e.g., as a closed-loop control system).

In some examples, display system 800 may display multiple virtual objects at once and may determine which virtual object a user is viewing (or is likely to be viewing) to identify a virtual object for which to correct the apparent accommodation distance. For example, the system may include an eye tracking system (not shown) that provides information to control element 822 to enable control element 822 to select the position of the relevant virtual object.

Additionally or alternatively, augmented reality logic 826 may provide information about which virtual object is the most important and/or most likely to draw the attention of the user (e.g., based on spatial or temporal proximity, movement, and/or a semantic importance metric attached to the virtual object). In some examples, the augmented reality logic 826 may identify multiple potentially important virtual objects and select an apparent accommodation distance that approximates the virtual distance of a group of the potentially important virtual objects.

Control system 820 may represent any suitable hardware, software, or combination thereof for managing adjustments to adjustable lenses 812. In some examples, control system 820 may represent a system on a chip (SOC). As such, one or more portions of control system 820 may include one or more hardware modules. Additionally or alternatively, one or more portions of control system 820 may include one or more software modules that perform one or more of the tasks described herein when stored in the memory of a computing device and executed by a hardware processor of the computing device.

Control system 820 may generally represent any suitable system for providing display data, augmented reality data, and/or augmented reality logic fora head-mounted display. In some examples, control system 820 may include a graphics processing unit (GPU) and/or any other type of hardware accelerator designed to optimize graphics processing.

Control system 820 may be implemented in various types of systems, such as the augmented reality glasses 900 illustrated in FIG. 9. As shown, glasses 900 may include adjustable-focus lenses 910 coupled to a frame 930 (e.g., at an eyewire, not shown). In some embodiments, control system 820 of FIG. 8 may be integrated into frame 930. Alternatively, all or a portion of control system 820 may be in a system remote from glasses 900 and configured to control electroactive devices (e.g., actuators) in glasses 900 via wired or wireless communication.

In an embodiment, each of lenses 910 may include, for example, an optical fluid encapsulated by an elastomeric membrane and an optically clear and rigid back substrate. Actuation along the perimeter of lenses 910 (e.g., using one or more electroactive devices as further shown and described in connection with FIGS. 1A-1C) may change the curvature (and thus the optical power) of the lenses, with positive and negative shapes determined by the direction of the applied force. In an embodiment, a membrane surface may be non-planar (e.g., concave or convex) at rest (e.g., at zero electrical power). In one example, a membrane surface may be non-planar when a substrate is curved.

Electroactive devices (e.g., actuators) mounted in frame 930 (e.g., in an eyewire) may deform each lens, with high optical quality achieved through tailored displacement and deflection, and via perimeter mounting for an asymmetric clear aperture including, for example, an RGB (red-green-blue) waveguide.

As noted, control system 820 of FIG. 8 may trigger electroactive devices to adjust lenses (e.g., lenses 910) to help address the vergence-accommodation conflict. The vergence-accommodation conflict may result from how humans perceive depth. When a human eye fixates on an object, it accommodates to that object—that is, it changes focal distance to bring that object into focus. That accommodation is a visual cue to depth: objects that are much closer or further away than that distance are out of focus on the retina. This "retinal blur" is a cue that objects are at a different distance than the accommodative distance, although the cue is ambiguous as to whether the objects are closer or more distant.

When both eyes are used (stereoscopically), binocular disparity is the main visual cue for depth. The two eyes look at an object from slightly different angles, so they get slightly different views of the object. This difference in views is the binocular disparity (imperfect match) between the two views. The visual system normally fuses these two images into a single perception and converts the disparity between the two images into a perception of depth. The closer an object is, the larger the disparity (error in matching) between the images it produces on the two retinas.

In a typical virtual reality head-mounted device, a virtual display plane, or focal plane, may be located at a fixed distance. But virtual objects may be "located" either in front of or behind the focal plane. The head-mounted display may try to reproduce binocular disparity for such virtual objects, which is the main visual cue for depth. But the binocular disparity cue may drive the eyes to verge at one distance, while the light rays coming from the virtual plane may produce retinal blur that drives the eyes to accommodate to another distance, creating a conflict between those depth cues and forcing the viewer's brain to unnaturally adapt to conflicting cues. This vergence-accommodation conflict in turn creates visual fatigue, especially during prolonged use of an augmented reality system.

As discussed throughout the instant disclosure, the disclosed devices, systems, and methods may provide one or more advantages over conventional devices, systems, and methods. For example, in contrast to prior devices, electroactive devices presented herein may include electroactive polymer elements that achieve substantially uniform strain in the presence of an electrostatic field produced by a potential difference between paired electrodes, permitting the electroactive devices to achieve, for example, improvements in both energy density and specific power density. Such uniform strain may reduce or eliminate unwanted deformations in the electroactive polymer elements and may result in greater overall deformation, such as compression, of the electroactive polymer elements, providing a greater degree of movement of surface regions of the electroactive polymer elements while requiring a lower amount of energy to provide such deformation. The electroactive polymer elements may include polymer materials having nanovoided regions that allow for additional compression in the presence of a voltage gradient in comparison to non-voided materials. Additionally, an electroactive device may be formed in a stacked structure having a plurality of electroactive polymer elements that are layered with multiple electrodes, enabling the plurality of electroactive polymer elements to be actuated in conjunction with each other in a single device that may undergo a more substantial degree of deformation (e.g., compression and/or expansion) in comparison to an electroactive device having a single electroactive polymer element or layer.

Electroactive devices described and shown herein may be utilized in any suitable technologies, without limitation. For example, such electroactive devices may be utilized as mechanical actuators to actuate movement of adjacent components. In at least one embodiment, the disclosed electroactive devices may be incorporated into optical systems such as adjustable lenses (e.g., fluid-filled lenses) as described herein to actuate movement of one or more optical layers.

Such actuation may, for example, allow for selected movement of lens layers of an adjustable lens, resulting in deformation of the lens layers to adjust optical characteristics (e.g., focal point, spherical correction, cylindrical correction, axial correction, etc.) of the adjustable lens. In some embodiments, electroactive devices as disclosed herein may be utilized as actuators in micromechanical apparatuses, such as microelectromechanical devices. Additionally or alternatively, electroactive devices may be used for converting mechanical energy to electrical energy for use in energy harvesting systems and/or sensor apparatuses.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

As detailed above, the computing devices, display devices, and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various embodiments of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A method comprising:
depositing a curable material onto a primary electrode;
curing the deposited curable material to form an electroactive polymer element comprising a cured elastomer material; and
depositing an electrically conductive material onto a surface of the electroactive polymer element opposite the primary electrode to form a secondary electrode;
wherein the cured elastomer material has a Poisson's ratio of between approximately 0.1 and approximately 0.35.

2. The method of claim 1, further comprising vaporizing the curable material, wherein depositing the curable material comprises depositing the vaporized curable material onto the primary electrode.

3. The method of claim 1, wherein depositing the curable material comprises printing the curable material onto the primary electrode.

4. The method of claim 1, further comprising curing the curable material with a source of radiation.

5. The method of claim 1, further comprising combining the curable material with particles of a material having a high dielectric constant.

6. The method of claim 1, further comprising:
depositing a monomer onto a surface of the secondary electrode opposite the electroactive polymer element;
curing the deposited monomer to form a second electroactive polymer element comprising a second cured elastomer material; and
depositing an additional electrically conductive material onto a surface of the second electroactive polymer element opposite the secondary electrode to form a tertiary electrode.

7. The method of claim 1, wherein the cured elastomer material comprises at least one of a silicone- or an acrylate-based polymer.

8. The method of claim 1, wherein curing the elastomer material comprises a siloxane polymer.

9. The method of claim 1, wherein curing the elastomer material includes an effective Poisson's ratio referring to a negative of the ratio of transverse strain to axial strain of the first elastomer material or the second elastomer material.

10. The method of claim 1, wherein curing the elastomer material includes a nanovoided material defining a plurality of voids having diameters of between approximately 10 nm and approximately 1000 nm.

11. A method comprising:
positioning a curable material between a first electrically conductive material and a second electrically conductive material; and
curing the positioned curable material to form an electroactive polymer element comprising a cured elastomer material;
wherein the cured elastomer material has a Poisson's ratio of between approximately 0.1 and approximately 0.35.

12. The method of claim 11, wherein:
at least one of the first electrically conductive material or the second electrically conductive material comprises a curable electrically conductive material; and
the method further comprises curing the at least one of the first electrically conductive material or the second electrically conductive material to form an electrode.

13. The method of claim 12, wherein curing the at least one of the first electrically conductive material or the second electrically conductive material comprises curing the at least one of the first electrically conductive material or the second electrically conductive material during curing of the positioned curable material.

14. The method of claim 11, wherein the curable material and at least one of the first electrically conductive material or the second electrically conductive material are flowable during positioning of the curable material between the first electrically conductive material and the second electrically conductive material.

15. The method of claim 14, further comprising flowing the curable material and the at least one of the first electrically conductive material or the second electrically conductive material simultaneously onto a substrate.

16. The method of claim 11, wherein the cured elastomer material comprises at least one of a silicone- or an acrylate-based polymer.

17. A method comprising:
depositing a first curable material onto a primary electrode;
curing the deposited first curable material to form a first electroactive polymer element comprising a cured first elastomer material;
depositing an electrically conductive material onto a surface of the first electroactive polymer element opposite the primary electrode to form a secondary electrode, wherein the first elastomer material is disposed between and abutting the primary electrode and the secondary electrode;
depositing a second curable material onto the secondary electrode;
curing the deposited second curable material to form a second electroactive polymer element comprising a cured second elastomer material; and
depositing another electrically conductive material onto a surface of the second electroactive polymer element opposite the secondary electrode to form a tertiary electrode, wherein the second elastomer material is disposed between and abutting the secondary electrode and the tertiary electrode;
wherein the first elastomer material and the second elastomer material each have a Poisson's ratio of between approximately 0.1 and approximately 0.35.

18. The method of claim 17, further comprising vaporizing the first curable material, wherein depositing the first curable material comprises depositing the vaporized first curable material onto the primary electrode.

19. The method of claim 17, further comprising curing the first curable material and the second curable material with a source of radiation.

\* \* \* \* \*